US012655473B2

(12) United States Patent
Fodor et al.

(10) Patent No.: US 12,655,473 B2
(45) Date of Patent: Jun. 16, 2026

(54) METHODS, COMPOSITIONS, AND SYSTEMS FOR MAPPING LOCATIONS OF SINGLE MOLECULES IN MULTI-DIMENSIONAL SPACE

(71) Applicant: Curio Bioscience, Inc., Palo Alto, CA (US)

(72) Inventors: Stephen P.A. Fodor, Palo Alto, CA (US); Hei Mun Christina Fan, Palo Alto, CA (US); Anaram Shahravan, San Jose, CA (US); Christina Chang, Palo Alto, CA (US); Jay Levine, San Leandro, CA (US)

(73) Assignee: Takara Bio USA, Inc., San Jose, CA (US)

( * ) Notice: Subject to any disclaimer, the term of this patent is extended or adjusted under 35 U.S.C. 154(b) by 0 days.

(21) Appl. No.: 18/492,620

(22) Filed: Oct. 23, 2023

(65) Prior Publication Data

US 2024/0052405 A1 Feb. 15, 2024

Related U.S. Application Data

(63) Continuation-in-part of application No. 17/895,633, filed on Aug. 25, 2022, which is a continuation of
(Continued)

(51) Int. Cl.
*C12Q 1/6841* (2018.01)
*C12Q 1/6804* (2018.01)
(Continued)

(52) U.S. Cl.
CPC ......... *C12Q 1/6841* (2013.01); *C12Q 1/6804* (2013.01); *G01N 33/5308* (2013.01);
(Continued)

(58) Field of Classification Search
CPC ................ C12Q 1/6804; C12Q 1/6841; G01N 33/5308; G01N 33/54326; G01N 2458/10; G01N 2570/00
See application file for complete search history.

(56) References Cited

U.S. PATENT DOCUMENTS

| | | | |
|---|---|---|---|
| 7,613,571 B2 | 11/2009 | Doyle et al. | |
| 8,053,744 B2 | 11/2011 | Bortolin | |
| (Continued) | | | |

FOREIGN PATENT DOCUMENTS

| | | |
|---|---|---|
| WO | WO-2009091934 A1 | 7/2009 |
| WO | WO-2010127186 A1 | 11/2010 |
| (Continued) | | |

OTHER PUBLICATIONS

Biermann et al. Dissecting the treatment-naive ecosystem of human melanoma brain metastasis. Cell 185(14):2591-2608.e30 (2022).
(Continued)

*Primary Examiner* — Jeremy C Flinders
(74) *Attorney, Agent, or Firm* — Fenwick & West LLP

(57) ABSTRACT

Systems, methods, and compositions for generating a high-resolution spatial map of a distribution of targets of a sample are described. Processes for generating the spatial map can include: receiving the sample at a substrate having a distribution of functionalized particles, each having a stochastic barcode sequence paired with a position on the substrate; promoting interactions between the distribution of targets of the sample and the distribution of functionalized particles upon transmitting heat to a surface of the substrate opposite the distribution of functionalized particles; applying a set of reactions to the sample at the substrate, obtaining a set of sequences of a population of molecules generated from the set of reactions, the set of sequences associated with the distribution of targets labeled using the stochastic barcode sequences of the distribution of functionalized particles, and
(Continued)

returning a set of positions of the distribution of targets upon processing the set of sequences.

18 Claims, 15 Drawing Sheets

Related U.S. Application Data application No. PCT/US2022/040859, filed on Aug. 19, 2022.

(60) Provisional application No. 63/235,304, filed on Aug. 20, 2021.

(51) Int. Cl.
*G01N 33/53* (2006.01)
*G01N 33/543* (2006.01)

(52) U.S. Cl.
CPC .................. *G01N 33/54326* (2013.01); *G01N 2458/10* (2013.01); *G01N 2570/00* (2013.01)

(56) References Cited

U.S. PATENT DOCUMENTS

| | | | |
|---|---|---|---|
| 8,124,362 | B2 | 2/2012 | Akhavan-Tafti |
| 8,835,358 | B2 | 9/2014 | Fodor et al. |
| 9,085,798 | B2 | 7/2015 | Chee |
| 9,290,808 | B2 | 3/2016 | Fodor et al. |
| 9,290,809 | B2 | 3/2016 | Fodor et al. |
| 9,315,857 | B2 | 4/2016 | Fu et al. |
| 9,476,101 | B2 | 10/2016 | Pregibon et al. |
| 9,567,645 | B2 | 2/2017 | Fan et al. |
| 9,567,646 | B2 | 2/2017 | Fan et al. |
| 9,598,736 | B2 | 3/2017 | Fan et al. |
| 9,637,799 | B2 | 5/2017 | Fan et al. |
| 9,708,659 | B2 | 7/2017 | Fodor et al. |
| 9,727,810 | B2 | 8/2017 | Fodor et al. |
| 9,783,847 | B2 | 10/2017 | Chee et al. |
| 9,816,137 | B2 | 11/2017 | Fodor et al. |
| 9,845,502 | B2 | 12/2017 | Fodor et al. |
| 10,000,800 | B2 | 6/2018 | Chee |
| 10,002,316 | B2 | 6/2018 | Fodor et al. |
| 10,030,261 | B2 | 7/2018 | Frisen et al. |
| 10,047,394 | B2 | 8/2018 | Fodor et al. |
| 10,059,991 | B2 | 8/2018 | Fodor et al. |
| 10,119,165 | B2 | 11/2018 | Chee |
| 10,131,958 | B1 | 11/2018 | Fan et al. |
| 10,151,003 | B2 | 12/2018 | Fan et al. |
| 10,202,646 | B2 | 2/2019 | Fodor et al. |
| 10,208,356 | B1 | 2/2019 | Fan et al. |
| 10,227,639 | B2 | 3/2019 | Levner et al. |
| 10,253,375 | B1 | 4/2019 | Fan et al. |
| 10,266,883 | B2 | 4/2019 | Chee |
| 10,266,884 | B2 | 4/2019 | Chee |
| 10,308,982 | B2 | 6/2019 | Chee |
| 10,392,661 | B2 | 8/2019 | Fodor et al. |
| 10,472,669 | B2 | 11/2019 | Chee |
| 10,480,022 | B2 | 11/2019 | Chee |
| 10,501,793 | B2 | 12/2019 | Chee |
| 10,619,203 | B2 | 4/2020 | Fodor et al. |
| 10,662,467 | B2 | 5/2020 | Chee |
| 10,662,468 | B2 | 5/2020 | Chee |
| 10,913,975 | B2 | 2/2021 | So et al. |
| 10,914,730 | B2 | 2/2021 | Chee |
| 10,927,419 | B2 | 2/2021 | Fan et al. |
| 10,954,570 | B2 | 3/2021 | Fan et al. |
| 10,961,566 | B2 | 3/2021 | Chee |
| 10,983,113 | B2 | 4/2021 | Chee |
| 10,996,219 | B2 | 5/2021 | Chee |
| 11,001,878 | B1 | 5/2021 | Chee |
| 11,001,879 | B1 | 5/2021 | Chee |
| 11,008,607 | B2 | 5/2021 | Chee |
| 11,021,737 | B2 | 6/2021 | Church et al. |
| 11,149,310 | B2 | 10/2021 | Fisher et al. |
| 11,162,132 | B2 | 11/2021 | Frisen et al. |
| RE48,913 | E | 2/2022 | Fodor et al. |
| 11,293,051 | B2 | 4/2022 | Church et al. |
| 11,293,052 | B2 | 4/2022 | Church et al. |
| 11,293,054 | B2 | 4/2022 | Levner et al. |
| 11,299,767 | B2 | 4/2022 | Church et al. |
| 11,299,774 | B2 | 4/2022 | Frisen et al. |
| 11,352,659 | B2 | 6/2022 | Frisen et al. |
| 11,390,912 | B2 | 7/2022 | Frisen et al. |
| 11,473,142 | B2 | 10/2022 | Beechem et al. |
| 11,479,809 | B2 | 10/2022 | Frisen et al. |
| 11,613,773 | B2 | 3/2023 | Frisen et al. |
| 11,618,929 | B2 | 4/2023 | Fan et al. |
| 11,624,088 | B2 | 4/2023 | Fan et al. |
| 11,702,706 | B2 | 7/2023 | Fan et al. |
| 12,168,226 | B2 | 12/2024 | West et al. |
| 2006/0040286 | A1 | 2/2006 | Mirkin et al. |
| 2006/0275782 | A1 | 12/2006 | Gunderson et al. |
| 2010/0105104 | A1 | 4/2010 | Okano et al. |
| 2010/0267015 | A1 | 10/2010 | Szasz |
| 2011/0212848 | A1 | 9/2011 | Duffy et al. |
| 2012/0065081 | A1 | 3/2012 | Chee |
| 2012/0289428 | A1 | 11/2012 | Duffy et al. |
| 2014/0194324 | A1 | 7/2014 | Gormley et al. |
| 2014/0243238 | A1 | 8/2014 | Seligmann et al. |
| 2015/0344942 | A1 | 12/2015 | Frisen et al. |
| 2016/0289740 | A1 | 10/2016 | Fu et al. |
| 2016/0312276 | A1 | 10/2016 | Fu et al. |
| 2016/0333403 | A1 | 11/2016 | Chee |
| 2017/0058339 | A1 | 3/2017 | Chee |
| 2017/0058340 | A1 | 3/2017 | Chee |
| 2017/0058345 | A1 | 3/2017 | Chee |
| 2017/0088881 | A1 | 3/2017 | Chee |
| 2017/0337459 | A1 | 11/2017 | Fodor et al. |
| 2018/0057873 | A1 | 3/2018 | Zhou et al. |
| 2018/0180601 | A1 | 6/2018 | Pedersen et al. |
| 2018/0251825 | A1 | 9/2018 | Stoeckius et al. |
| 2019/0262831 | A1 | 8/2019 | West et al. |
| 2019/0309355 | A1 | 10/2019 | Chee |
| 2020/0048701 | A1 | 2/2020 | Chee |
| 2020/0048702 | A1 | 2/2020 | Chee |
| 2020/0048703 | A1 | 2/2020 | Chee |
| 2020/0224266 | A1 | 7/2020 | Fodor et al. |
| 2020/0354788 | A1 | 11/2020 | Fodor et al. |
| 2020/0391210 | A1 | 12/2020 | Handique |
| 2021/0062272 | A1 | 3/2021 | Williams et al. |
| 2021/0095331 | A1 | 4/2021 | Fan et al. |
| 2021/0123040 | A1 | 4/2021 | Macosko et al. |
| 2021/0155982 | A1 | 5/2021 | Yin et al. |
| 2021/0164039 | A1 | 6/2021 | Wang et al. |
| 2021/0214785 | A1 | 7/2021 | Stoecki |
| 2021/0230681 | A1 | 7/2021 | Patterson et al. |
| 2021/0238670 | A1 | 8/2021 | Chee |
| 2021/0238671 | A1 | 8/2021 | Chee |
| 2021/0238675 | A1 | 8/2021 | Bava |
| 2021/0262019 | A1 | 8/2021 | Alvarado Martinez et al. |
| 2021/0265017 | A1 | 8/2021 | Dutta et al. |
| 2021/0382061 | A1 | 12/2021 | Yun et al. |
| 2022/0010367 | A1 | 1/2022 | Ramachandran Iyer et al. |
| 2022/0017952 | A1 | 1/2022 | Fan et al. |
| 2022/0033805 | A1 | 2/2022 | Srivatsan et al. |
| 2022/0119871 | A1 | 4/2022 | Regev et al. |
| 2022/0180975 | A1 | 6/2022 | Regev et al. |
| 2022/0220555 | A1 | 7/2022 | Beechem et al. |
| 2022/0251632 | A1 | 8/2022 | Regier et al. |
| 2023/0057339 | A1 | 2/2023 | Fodor et al. |
| 2023/0212659 | A1 | 7/2023 | Fan et al. |
| 2024/0344118 | A1 | 10/2024 | Chang et al. |

FOREIGN PATENT DOCUMENTS

| | | | |
|---|---|---|---|
| WO | WO-2012140224 | A1 | 10/2012 |
| WO | WO-2014060483 | A1 | 4/2014 |
| WO | WO-2016162309 | A1 | 10/2016 |
| WO | WO-2017075293 | A1 | 5/2017 |
| WO | WO-2019199579 | A1 | 10/2019 |
| WO | WO-2019213254 | A1 | 11/2019 |
| WO | WO 2020/123320 | A2 | 6/2020 |
| WO | WO-2020123309 | A1 | 6/2020 |

(56)                References Cited

FOREIGN PATENT DOCUMENTS

| WO | WO 2020/160044 | A1 | 8/2020 |
| WO | WO-2021096814 | A1 | 5/2021 |
| WO | WO-2022015925 | A1 | 1/2022 |
| WO | WO-2023023308 | A1 | 2/2023 |
| WO | WO-2024020395 | A2 | 1/2024 |
| WO | WO-2024206652 | A2 | 10/2024 |

OTHER PUBLICATIONS

Choe et al. Advances and Challenges in Spatial Transcriptomics for Developmental Biology. Biomolecules 13(1):156 (2023).

Di Bella et al. Molecular logic of cellular diversification in the mouse cerebral cortex. Nature 595(7868):554-559 (2021).

Dong et al. Deciphering spatial domains from spatially resolved transcriptomics with an adaptive graph attention auto-encoder. Nat Commun 13(1):1739 (2022).

Fan et al. Combinatorial labeling of single cells for gene expression cytometry. Science 347:1258367 (2015).

Huang et al.: Centrifugal micro-channel array droplet generation for highly parallel digital PCR. Lap on a Chip 17(2):235-240 (2017).

Kamath et al. Single-cell genomic profiling of human dopamine neurons identifies a population that selectively degenerates in Parkinson's disease. Nat Neurosci 25(5):588-595 (2022).

Li et al. A comprehensive benchmarking with practical guidelines for cellular deconvolution of spatial transcriptomics. Nat Commun 14(1):1548 (2023).

Mantri et al. Spatiotemporal transcriptomics reveals pathogenesis of viral myocarditis. Nat Cardiovasc Res. 1(10):946-960 (2022).

Marshall et al. High-resolution Slide-seqV2 spatial transcriptomics enables discovery of disease-specific cell neighborhoods and pathways. iScience 25(4):104097 (2022).

Moses et al. Museum of spatial transcriptomics. Nat Methods 19(5):534-546 (2022).

[No Authors Listed] Method of the Year 2020: spatially resolved transcriptomics. Nat Methods 18(1):1 (2021).

Noel et al. Principles of Spatial Transcriptomics Analysis: A Practical Walk-Through in Kidney Tissue. Front Physiol 12:809346 (2022).

Palla et al. Squidpy: a scalable framework for spatial omics analysis. Nat Methods 19(2):171-178 (2022).

PCT/US2021/041741 International Search Report and Written Opinion dated Dec. 16, 2021.

PCT/US2022/040859 International Invitation to Pay Additional Fees dated Nov. 3, 2022.

PCT/US2022/040859 International Search Report and Written Opinion dated Jan. 9, 2023.

Rodriques et al. Slide-seq: A scalable technology for measuring genome-wide expression at high spatial resolution. Science 363(6434):1463-1467 (2019).

Rodriques et al. Slide-seq: A scalable technology for measuring genome-wide expression at high spatial resolution. Science 363(6434):1463-1467 (Supplementary Material) (2019).

Shen et al. Recent advances in high-throughput single-cell transcriptomics and spatial transcriptomics. Lab on a Chip 22:4774 (2022).

Soto et al. Controlled assembly of mesoscale structures using DNA as molecular bridges. J Am Chem 124:8508-8509 (2002).

Stahl, et al. Visualization and analysis of gene expression in tissue sections by spatial transcriptomics. Science. Jul. 1, 2016;353(6294):78-82. doi: 10.1126/science.aaf2403.

Stickels et al. Highly sensitive spatial transcriptomics at near-cellular resolution with Slide-seqV2. Nat Biotechno 39(3):313-319 (2021).

U.S. Appl. No. 17/376,396 Office Action dated Apr. 22, 2022.

U.S. Appl. No. 17/895,633 Office Action dated Apr. 6, 2023.

U.S. Appl. No. 17/895,633 Office Action dated Oct. 12, 2023.

U.S. Appl. No. 17/895,633 Restriction Requirement dated Dec. 23, 2022.

Valignet et al. Reversible self-assembly and directed assembly of DNA-linked micrometer-sized colloids. PNAS USA 102(12):4225-4229 (2005).

Van Den Brink et al. Single-cell sequencing reveals dissociation-induced gene expression in tissue subpopulations. Nat Methods 14(10):935-936 (2017).

Vickovic, et al. High-definition spatial transcriptomics for in situ tissue profiling. Nature methods 16.10 (2019): 987-990.

Wang et al. Spatial transcriptomic reconstruction of the mouse olfactory glomerular map suggests principles of odor processing. Nat Neurosci 25(4):484-492 (2022).

Williams et al. An introduction to spatial transcriptomics for bio-medical research. Genome Med 14(1):68 (2022).

Xu et al. CoSTA: unsupervised convolutional neural network learning for spatial transcriptomics analysis. BMC Bioinformatics 22(1):397 (2021).

Yu et al. Spatial transcriptomics technology in cancer research. Front Oncol 12:1019111 (2022).

Armani, M. et al., 2D-PCR: a method of mapping DNA in tissue sections, Lab Chip, 9:3526-3534 (2009).

Southern, E.M. et al. Arrays of complementary oligonucleotides for analysing the hybirdisation behaviour of nucleic acids. Nucleic Acids Research 22(8):1368-1373 (1994).

Southern, E.M. et al, DNA chips: analysing sequence by hybridization to oligonucleotides on a large scale. Technical Focus 12(3):110-5 (1996).

Curio. Curio Seeker Spatial Mapping Kit. Dec. 31, 2023; [retrieved on Sep. 30, 2024]. Available at URL:https://curiobioscience.com/documentation/ pp. 1-4.

Federal Register 84(4):35-64 (2019).

Kim, H. et al. Nuclear oligo hashing improves differential analysis of single-cell RNA-seq. Nature Communications; 13:2666 (2022).

Lee, Y. et al. XYZeq: Spatially resolved single-cell RNA sequencing reveals expression heterogeneity in the tumor microenvironment. Sci. Adv., 7(17):eabg4755 (2021).

Leigh, Nicholas. et al. RNA in situ hybridization. Nature Communications:1-19 (2018).

PCT/US2024/022002 International Search Report and Written Opinion dated Sep. 4, 2024.

PCT/US2024/022002 Invitation to Pay Additional Fees dated Jun. 14, 2024.

PCT/US2024/034537 International Search Report and Written Opinion dated Oct. 25, 2024.

Russell, Andrew JC. et al. Slide-tags Enables Single-nucleus Barcoding for Multimodal Spatial Genomics. Nature 625(7993):101-109 (2024). Published Online Dec. 13, 2023.

Srivatsan, S. et al. Embryo-scale, single cell spatial transcriptomics. Science. Author manuscript; pp. 16 (2022).

U.S. Appl. No. 18/622,603 Office Action dated Nov. 5, 2024.

European Patent Office, EP21841253.4 Supplementary Search Report dated May 2, 2024.

U.S. Appl. No. 17/376,396 Notice of Allowance dated Dec. 7, 2022.

Yanyi Huang et al., Centrifugal micro-channel array droplet generation for highly parallel digital PCR, Lab on a Chip, Jan. 21, 2017, pp. 235-240, vol. 17, No. 2, Royal Society of Chemistry, London, UK.

European Patent Office, Extended European Search Report, EP Patent Application No. 22859206.9, May 15, 2025, 23 pages.

Sample

Protrusion

Substrate 110

Recess

Substrate 110

Close-packed particles

**Spotted features with gap
Between centers of features**

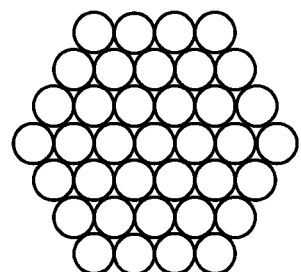

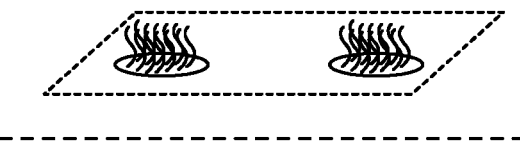

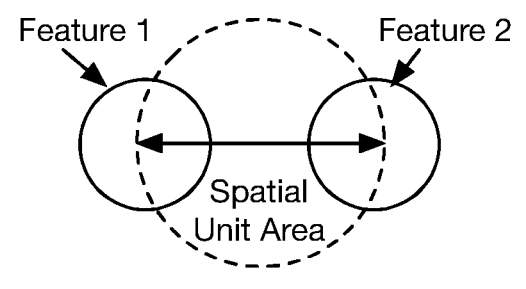

Feature 1                    Feature 2

Spatial Unit Area

- Smaller area per feature
- Higher resolution
- Smaller Spatial Unit Area
- Smaller Functional Unit Area
- Less leakage/background noise
- Ability to identify features (e.g., single cell subtypes) without deconvolution, referencing single cell databases Functional Unit Area

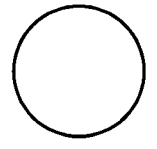

- Greater area per feature
- Lower resolution
- Larger Spatial Unit Area
- Larger Functional Unit Area
- More leakage/background noise
- Inability to identify features (e.g., single cell subtypes) without deconvolution, referencing single cell databases

FIG. 1C

Support Structure 200

Operation Modes

Magnetic component
24

Wand 25

Cage/
Cassette 26

Support Structure 200b

Support Structure 200b

Tip
210b

Sample

Method of
Manufacture 300
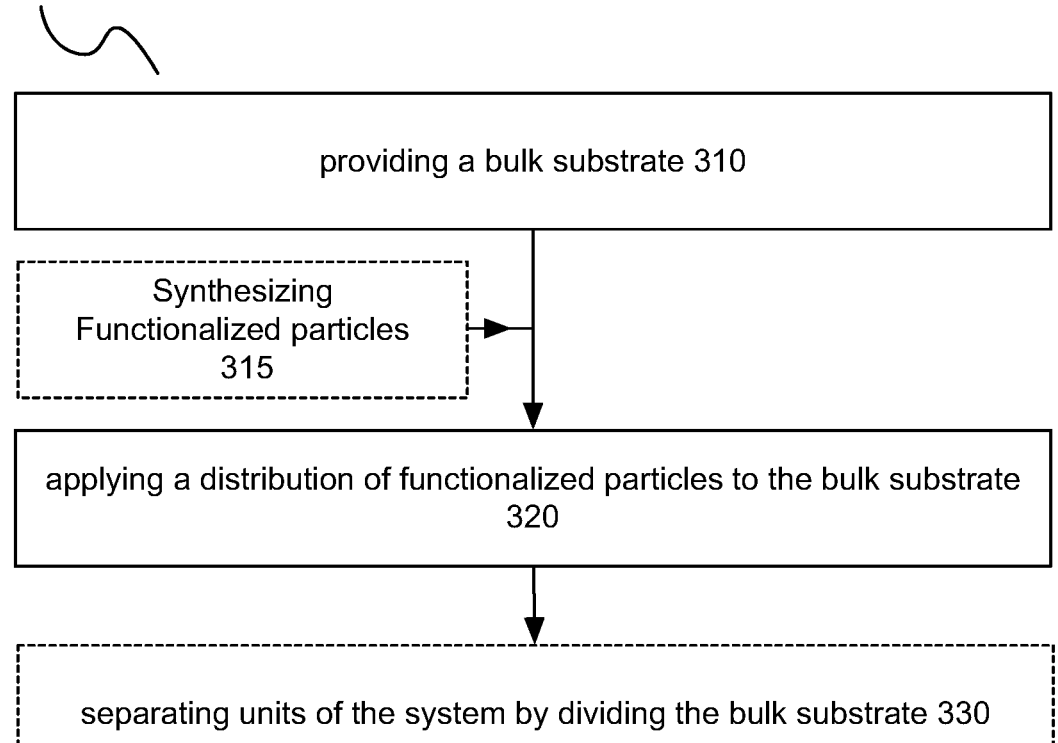
providing a bulk substrate 310
Synthesizing
Functionalized particles
315
applying a distribution of functionalized particles to the bulk substrate
320
separating units of the system by dividing the bulk substrate 330
FIG. 6
Template Variations
FIG. 7A
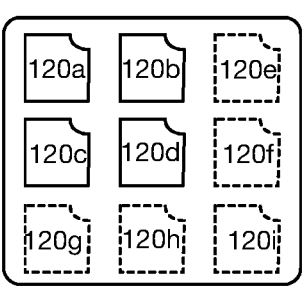
| 120a | 120b | 120e |
| 120c | 120d | 120f |
| 120g | 120h | 120i |
FIG. 7B Separating Units
330

Method 400

420'

Medium (e.g., hydrogel, polaxomer)

Single Cell/Particle/Analyte

Variation of substrate with
Distribution of functionalized particles

METHODS, COMPOSITIONS, AND SYSTEMS FOR MAPPING LOCATIONS OF SINGLE MOLECULES IN MULTI-DIMENSIONAL SPACE

CROSS-REFERENCE

This application is a continuation-in-part of U.S. patent application Ser. No. 17/895,633, filed Aug. 25, 2022, which is a continuation of PCT/US2022/040859, filed Aug. 19, 2022, which claims the benefit of U.S. Provisional Application No. 63/235,304, filed Aug. 20, 2021, each of which applications is incorporated in its entirety herein by this reference.

TECHNICAL FIELD

This invention relates generally to the sample characterization field, and more specifically to new and useful systems, methods, and compositions for characterizing locations of target analytes.

BACKGROUND

With an increased interest in understanding distributions of particular target analytes within a biological sample, improved compositions, methods, and systems that allow for analyte mapping are becoming highly valuable. Current technologies are limited in resolution (e.g., with respect to location of target analytes), ability to characterize locations in multiple dimensions, ability to characterize locations across scales of magnitude, ability to characterize different types of analytes, ability to characterize locations of targets in situ, and/or in other manners. Furthermore, compositions for enabling mapping can require high precision and uniformity in composition in order to enable accurate characterization of target locations in space. Thus, there is a need in the sample characterization field for new and useful systems, methods, and compositions for characterizing locations of target analytes.

SUMMARY OF THE INVENTION

Currently, methods and systems for spatially resolving single or multiple analytes in space (e.g., in situ, in vitro, etc.) are limited in relation to: resolution (e.g., with respect to potential number of target analytes that can be characterized per unit area or volume, with respect to scale of position determination for target analytes), low signal to noise ratio (e.g., due to high levels of background noise), empty/unused space between individual sites for target analytes interactions, ability to characterize locations in multiple dimensions, ability to characterize locations across scales of magnitude, ability to characterize different types of analytes, ability to characterize single cell subtypes without referencing single cell databases (e.g., using spatial marker genes alone), ability to characterize locations of targets in situ, ability to characterize locations of targets in vitro, and/or in other manners.

Accordingly, this disclosure describes embodiments, variations, and examples of systems, methods, and compositions for performing spatial biology (e.g., spatial transcriptomics, spatial proteomics, spatial multi-omics, etc.), in a manner that provides broader transcriptome coverage while achieving high levels of spatial resolution.

An aspect of the disclosure provides embodiments, variations, and examples of systems, methods, and compositions for efficient capture and labeling of target material (e.g., DNA, RNA, miRNA, proteins, small molecules, single analytes, multianalytes, etc.) to enable analyses for characterizing locations of target material in space. For nucleic acid targets, capture probes of compositions described can include complementary molecules to the nucleic acid targets. For protein targets or small molecule targets, capture probes of the compositions described can include antibodies or aptamers conjugated with specific nucleic acid sequences for detection.

Aspects of the disclosure also provide embodiments, variations, and examples of systems, methods, and compositions for generating spatial maps of a set of targets of a sample, where the spatial maps have a resolution of greater than one target mapped per 500 um$^2$, greater than one target mapped per 400 um$^2$, greater than one target mapped per 300 um$^2$, greater than one target mapped per 200 um$^2$, greater than one target mapped per 150 um$^2$, greater than one target mapped per 100 um$^2$, greater than one target mapped per 50 um$^2$, greater than one target mapped per 40 um$^2$, greater than one target mapped per 30 um$^2$, greater than one target mapped per 20 um$^2$, greater than one target mapped per 10 um$^2$, greater than one target mapped per 9 um$^2$, greater than one target mapped per 8 um$^2$, greater than one target mapped per 7 um$^2$, or any intermediate number of targets mapped per unit area.

Mapping can be performing for each of a set of at least 2 targets, 3 targets, 4 targets, 5 targets, 6 targets, 7 targets, 8 targets, 9 targets, 10 targets, 11 targets, 12 targets, 13 targets, 14 targets, 15 targets, 16 targets, 17 targets, 18 targets, 19 targets, 20 targets, 25 targets, 30 targets, 40 targets, 50 targets, 100 targets, 500 targets, 1000 targets, 5000 targets, 10000 targets, 15000 targets, 20000 targets, 30000 targets, 40000 targets, 50000 targets, 100000 targets, or any intermediate number of targets simultaneously, at resolutions described.

Generated maps can have an associated signal-to-noise ratio (SNR) of at least 100, 200, 300, 400, 500, 600, 700, 800, 900, 1000, 2000, 3000, 4000, 5000, 6000, 7000, 8000, 9000, 10000, 100000, or greater, where background noise is attributed to leakage of targets away from their original positions at the sample and toward functionalized particles that are positioned further away from the original positions at the sample. As such, SNR can be determined by calculating a ratio between a number of signal copies observed at "correct" positions and a number of background copies of targets present in "background" positions). In variations, determining the SNR can include: identifying one or a set of genes known to be expressed in regions (e.g., single cell types, single cell subtypes) of a sample (where such genes can be expressed at low level, such as less than 100 copies per particle, or at high level); quantifying expression of the one gene or the set of genes across the sample (e.g., according to method steps described below), determining a value of the signal from a measure of the expression of the one gene or the set of genes in regions that should express such gene(s), and determining a value of the noise from a measure of the expression of the one gene or the set of genes in regions that should not express such genes. The SNR can then be determined from the value of the signal divided by the value of the noise. In a specific example, for a mouse hippocampus sample, the SNR was determined using hippocalcin hpca) gene and transthyretin (ttr) gene, which are known to be expressed by certain hippocampus cell subtypes and not represented in other sample regions. Using hpca and ttr, the value of the noise was determined to be 0, indicating that hpca and ttr genes were not observed in regions that should not express hpca/ttr. As such, the SNR for the example sample type was shown to be infinite. Values of signal and noise can be determined from raw or normalized counts. Higher levels of noise can be attributed to anchoring of oligonucleotides onto glass substrates directly (e.g., without a particle layer intermediary), which can create different surface physical characteristics that promote target leakage and thus greater levels of background noise.

Generated maps can have an associated false positive rate less than a threshold number (e.g., a false positive percentage), where the false positive rate is determined from a percent (e.g., x %) of positive copies of targets observed beyond a threshold distance (e.g., y micrometers) away from where the positive copies ("signal") should actually originate from. In examples, the false positive rate can be less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, or less than another suitable percent. In examples, the threshold distance can be 15 micrometers, 14 micrometers, 13 micrometers, 12 micrometers, 11 micrometers, 10 micrometers, 9 micrometers, 8 micrometers, 7 micrometers, 6 micrometers, 5 micrometers, 4 micrometers, 3 micrometers, 2 micrometers, or another suitable threshold distance, where background noise is attributed to leakage of targets away from their original positions at the sample and toward functionalized particles that are positioned further away from the original positions at the sample.

Aspects of the disclosure also provide embodiments, variations, and examples of systems for generating spatial maps of a set of targets of a sample, where the empty/unused space between substrate features (e.g., beads or other particle bodies, rods, protrusions, recesses, ridges, valleys, channels, wells, oligonucleotide spots, etc.) for generating such spatial maps is less than 45 micrometers, 40 micrometers, 35 micrometers, 30 micrometers, 25 micrometers, 20 micrometers, 15 micrometers, 10 micrometers, 9 micrometers, 8 micrometers, 7 micrometers, 6 micrometers, 5 micrometers, 5 micrometers, 4 micrometers, 3 micrometers, 2 micrometers, 1 micrometer, 0.5 micrometers, 0.25 micrometers, 0.1 micrometers, or intermediate distances.

Aspects of the disclosure also provide embodiments, variations, and examples of systems, methods, and compositions for generating spatial maps of a set of targets of a sample, where the spatial maps have a resolution of less than a threshold distance between features (e.g., beads or other particle bodies, rods, protrusions, recesses, ridges, valleys, channels, wells, oligonucleotide spots, etc.) of a substrate for target capture/interactions. Embodiments, variations, and examples of spatial maps generated have a resolution of less than 50 picometers between features, less than 40 picometers between features, less than 30 picometers between features, less than 20 picometers between features, less than 10 picometers between features, less than 5 picometers between features, or less than 1 picometer between features.

In particular, in relation to platforms involving non-close-packed features (e.g., functionalized particles) for target capture and mapping, the invention(s) described achieve high resolution mapping with minimal (or non-existent noise, as described above), by having smaller functional unit areas and spatial unit areas for target capture. Furthermore, the systems described minimize the amount of empty or dead space between features for target capture, by close packing such features (e.g., in comparison to platforms where features are printed as spots that are spaced apart at the surface of a substrate, such as a glass slide). In examples, as shown in FIG. 1C, structural configurations of the features for target mapping, as in the inventions described, produce smaller capture areas per feature (and therefore higher resolution data), smaller spatial unit areas, smaller functional unit areas, less leakage of targets from the sample and therefore lower levels of background noise, and the ability to identify features (e.g., single cell subtypes) based upon a clustering analysis of spatial biomarkers, and without requiring deconvolution or other more involved computational approaches.

Aspects of the disclosure provide embodiments, variations, and examples of systems, methods, and compositions for spatially characterizing samples in multidimensions (e.g., 2D, 3D, 4D with a time component), in relation to one or more of: whole tissue structures, tissue pieces (e.g., as in histology, in relation to biopsied tissues, in relation to seeded natural scaffolds, in relation to seeded synthetic scaffolds (e.g., cell-seeded hydrogel scaffolds, cell-seeded polaxamer scaffolds, etc.) in relation to frozen tissue specimens, in relation to formalin-fixed and paraffin-embedded (FFPE) specimens, fresh frozen plasma etc.), frozen cell suspensions, cell suspensions retained in a medium/hydrogel medium organs, whole organisms, organoids, cell suspensions, single cells, organelles, sub-organelle structures, intra-organelle components, viruses, microorganisms, and other natural structures.

Location characterization can additionally or alternatively be performed in relation to non-naturally occurring structures, such as microwells, microarrays, scaffolds, and other non-naturally occurring structures. For instance, the invention(s) can have in situ and/or in vivo applications, with infusion of functionalized particles into a sample (e.g., into a cell, into a tissue, into an organ, etc.). Examples of infusion can include one or more of: injection, electroporation, use of vectors (e.g., viral vectors), and other infusion methods.

In relation to single cell characterizations associated with various tissue types or other sample types, aspects of the disclosure provide embodiments, variations, and examples of methods for generating a spatial map of single cell subtypes of the sample based upon spatial biomarkers alone (e.g., without referencing single cell reference databases). In particular, given particle sizes implemented in the invention(s) described, single cell subtypes can be determined using unsupervised clustering architecture, without requiring deconvolution (e.g., which is used when the functional area for target capture is larger (e.g., larger than 20 microns)). Examples of the methods described are able to achieve identification of microglia, endothelial cells, astrocyte subtypes, interneurons, neurons, oligodendrocytes, polydendrocytes, entorihinal, ependymal, choroid, neurogenesis, cajal retzius, mural, and other tissue cell subtypes by applying a clustering analysis to marker genes alone.

Aspects of the disclosure provide embodiments, variations, and examples of methods for generating a spatial map of a distribution of targets of a sample by a set of processes, where the set of processes can include: receiving a sample at a substrate comprising a distribution of functionalized particles, each of the distribution of functionalized particles including a stochastic barcode sequence paired with a position on the substrate (with decoding of the positions of the stochastic barcode sequences prior to use for target mapping); promoting interactions between the distribution of targets of the sample and the distribution of functionalized particles (e.g., upon transmitting heat to a surface of the substrate opposite the distribution of functionalized particles for frozen samples); applying a set of reactions to the sample at the substrate; obtaining a set of sequences of a population of molecules generated from the set of reactions, the set of sequences associated with the distribution of targets labeled using the stochastic barcode sequences of the distribution of functionalized particles, and returning a set of positions of the distribution of targets upon processing the set of sequences.

Aspects of the disclosure also provide embodiments, variations, and examples of systems, methods, and compositions configured for high levels of parallel sample processing, where, upon receiving a sample at a substrate, the sample can be re-frozen (e.g., at 0° C., at –20° C., at –80° C., etc.) for a duration of time prior to performing subsequent processing steps (e.g., post-thaw) for target mapping, without significant degradation in mapping performance (e.g., in relation to performance and quality metrics described).

In relation to quality metrics, aspects of the disclosure also provide embodiments, variations, and examples of systems, methods, and compositions that achieve threshold levels of performance in relation to various quality metrics. In examples, the invention(s) can achieve one or more of: number of paired end sequencing reads greater than a threshold level (e.g., greater than 100,000,000, greater than 200,000,000, greater than 500,000,000, etc.); percentage of read pairs having proper structure greater than a threshold percentage (e.g., 60%, 70%, 80%, 90%, 99%, etc.), where proper structure is determined by comparing the read sequence to the actual synthesized sequence (e.g., order of barcode regions, universal primer regions, unique molecule identifiers, polyT tails, etc.); total number of barcode sequences read per substrate greater than a threshold (e.g., 40,000, 50,000, 60,000, 70,000, 80,000, 90,000, 100,000, etc.); percentage of barcode sequences recovered greater than a threshold (e.g., 60%, 70%, 80%, 90%, 99%, etc.); percent of proper reads matched to a barcode sequence greater than a threshold (e.g., 60%, 70%, 80%, 90%, 99%, etc.); percent of proper reads in genes greater than a threshold (e.g., 60%, 70%, 80%, 90%, 99%, etc.); percent of proper reads matched to barcode sequences and genic sequences greater than a threshold (e.g., 60%, 70%, 80%, 90%, 99%, etc.); percent of raw useful reads (matched to a barcode sequences and genic sequences) greater than a threshold (e.g., 30%, 40%, 50%, 60%, 70%, 80%, 90%, 99%, etc.); average reads per unique molecule identifier (UMI) satisfying a threshold condition; total number of genes in matched bead barcodes greater than a threshold (e.g., 5,000, 10,000, 15,000, 20,000, 25,000, 30,000, 35,000, 40,000, 50,000, etc.); total number of UMIs in matched bead barcodes greater than a threshold (e.g., greater than 5,000, 000, 10,000,000, 15,000,000, 20,000,000, 25,000,000, etc.); average reads per bead greater than a threshold (e.g., 100, 200, 300, 400, 500, 600, 700, 800, 900, 1000, etc.); average number of UMIs per bead greater than a threshold (e.g., 100, 200, 300, 400, 500, 600, 700, 800, 900, 1000, etc.); average number of genes per bead greater than a threshold (e.g., 100, 200, 300, 400, 500, 600, 700, 800, 900, 1000, etc.); top percents of reads, UMIs, and/or genes per bead greater than a threshold (e.g., 100, 200, 300, 400, 500, 600, 700, 800, 900, 1000, etc.); average percent of mitochondrial UMIs per bead satisfying a threshold condition; average percent of ribosomal protein UMIs per bead satisfying a threshold condition; average percent of ribosomal RNA UMIs per bead satisfying a threshold condition; and/or other suitable quality metrics.

Aspects of the disclosure also provide embodiments, variations, and examples of systems, methods, and non-naturally-occurring compositions for facilitating capture of target biological material from a sample and characterizing locations of target biological material in space (e.g., two dimensional space, three dimensional space). Such compositions can include materials that have been modified from their natural states (e.g., in terms of providing structural differences from natural compositions). Furthermore, the invention(s) relate to combinations of materials, where the combinations of materials are non-naturally occurring (e.g., there is no naturally occurring counterpart to the compositions described and claimed).

Aspects of the disclosure also provide embodiments, variations, and examples of improved manufacturing methods for generating systems for characterizing locations of target analytes in space, in relation to efficiently generating multiple system units for kitting purposes.

Aspects of the disclosure also provide embodiments, variations, and examples of systems, methods, and compositions for location characterization in multiple dimensions, where particles of the composition(s) described can be implemented in monolayer form (e.g., with manufacturing processes to apply composition units in monolayer or near-monolayer form, with systems that apply magnetic or other forces to form particle monolayers, etc.), with sample (e.g., tissue, cells) positioned adjacent the monolayer for subsequent processing and mapping. Alternatively, particles of the composition(s) described can be infused into a sample/specimen (e.g., by magnetic force, by electroporation, by using vectors, etc.). Alternatively, particles of the composition(s) described can be coupled to a surface of a sample/specimen (e.g., by chemical binding, by magnetic binding, by other binding), in order to enable surface mapping. Alternatively, particles of the composition(s) described can be guided or otherwise retained in 3D structures (e.g., in grids, in non-grid structures), such as microwells, microarrays (e.g., with nucleic acids capturing particles), scaffolds (e.g., hydrogels), or other 3D structures. In a related application, physical or other forces can be used to define structures (e.g., close packed structures) for distributions of particles that interact with samples to enable mapping. Alternatively, in relation to location characterization in multiple dimensions, particles of composition(s) described can be randomly distributed in space.

Aspects of the disclosure also provide embodiments, variations, and examples of systems, methods, and compositions for applications in spatial transcriptomics. Compositions, methods, and systems described can be used for mapping of targets in a sample over time, in order to understand disease pathology and progression (e.g., spread of targets and changes in expression over time).

Additional aspects and advantages of the present disclosure will become readily apparent to those skilled in this art from the following detailed description, wherein only illustrative embodiments of the present disclosure are shown and described. The present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference. Furthermore, where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

BRIEF DESCRIPTION OF THE DRAWINGS

FIG. 1C depicts variations of structural features for target capture and spatial mapping, with resulting performance differences.

FIG. 6 depicts a flowchart of an embodiment of a method of manufacturing a system for characterizing locations of target analytes in space.

FIG. 7A depicts variations of templates used in manufacturing a system for characterizing locations of target analytes in space.

FIG. 7B depicts a variation of a substrate with multiple distributions of functionalized particles.

DETAILED DESCRIPTION OF THE INVENTION(S)

Figure 1A:
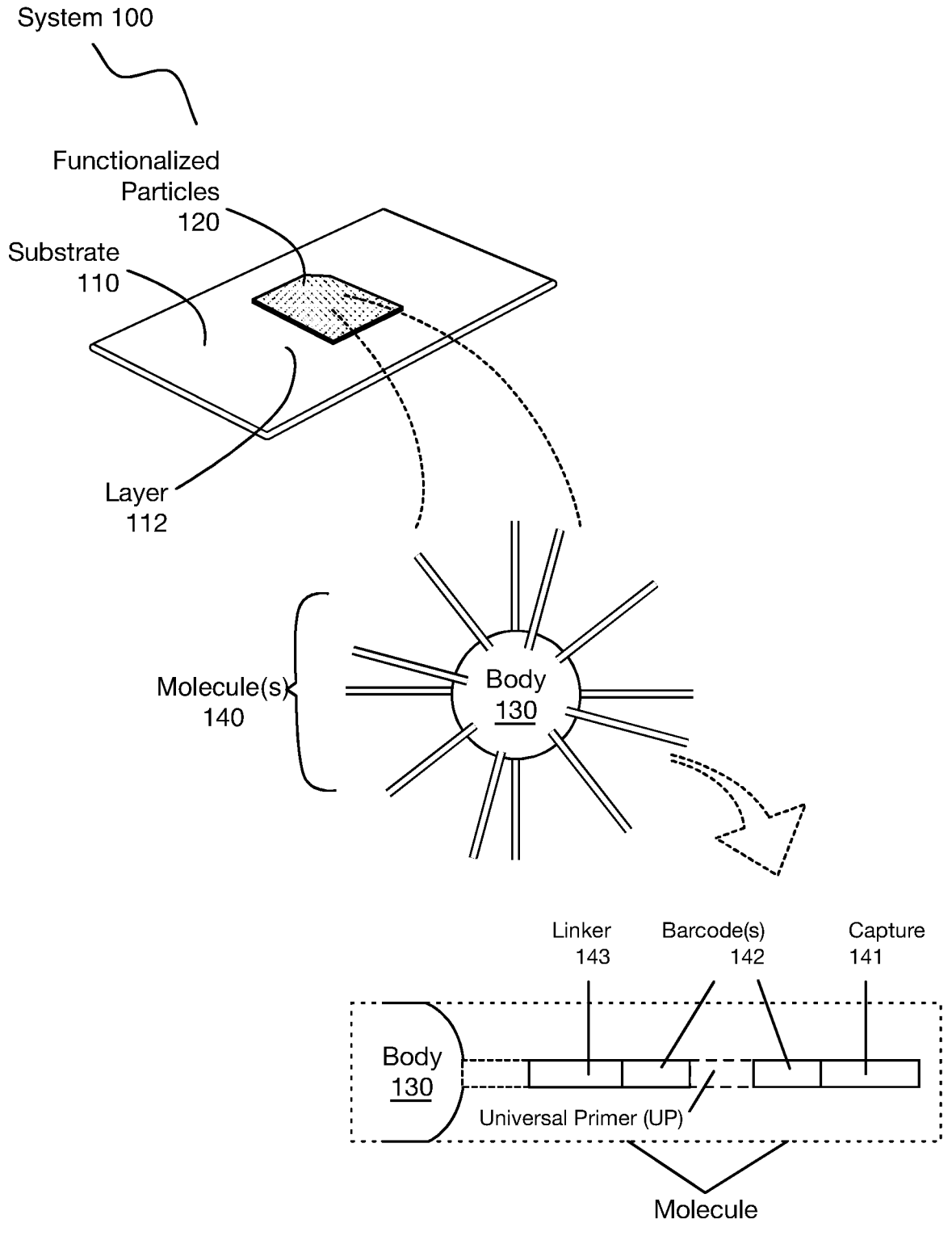
FIG. 1A depicts a schematic of an embodiment of a system for characterizing locations of target analytes in space.

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

1. General Overview

The present disclosure covers systems, devices, methods performed by such systems and devices, and methods of manufacturing and assembling such devices.

Generally, embodiments of the methods, systems, and compositions provide mechanisms for efficient capture and labeling of target material (e.g., DNA, RNA, miRNA, proteins, small molecules, single analytes, multianalytes, etc.) in order to enable analyses for characterizing locations of target material in space. For nucleic acid targets, capture probes of compositions described can include complementary molecules to the nucleic acid targets. For protein targets or small molecule targets, capture probes of the compositions described can include antibodies or aptamers conjugated with specific nucleic acid sequences for detection.

The systems, methods, and devices disclosed herein can provide several additional benefits over other systems and methods, and such systems, methods, and devices are further implemented into many practical applications across various disciplines.

The systems, methods, and devices can generate spatial maps of a set of targets of a sample, where the spatial maps have unprecedented resolution performance, ability to map multiple sets of targets for different sample and tissue types, and satisfy quality metrics for high resolution mapping.

The systems, methods, and devices also are designed to promote ease of use by end user(s), in relation to processing different tissue types and/or various sample types (e.g., involving natural and synthetic scaffolds).

The systems, methods, and devices provide and implement non-naturally occurring compositions for facilitating capture of target biological material from a sample and characterizing locations of target biological material in space (e.g., two dimensional space, three dimensional space). Such compositions can include materials that have been modified from their natural states (e.g., in terms of providing structural differences from natural compositions). Furthermore, the invention(s) relate to combinations of materials, where the combinations of materials are non-naturally occurring (e.g., there is no naturally occurring counterpart to the compositions described and claimed).

The systems, methods, and devices provide improved manufacturing methods for generating systems for characterizing locations of target analytes in space.

The systems, methods, and devices provide improved characterization of locations of targets in multidimensions (e.g., 2D, 3D, 4D with a time component), in relation to one or more of: whole tissue structures, tissue pieces (e.g., as in histology, in relation to biopsied tissues, in relation to seeded natural scaffolds, in relation to seeded synthetic scaffolds (e.g., cell-seeded hydrogel scaffolds, cell-seeded polaxamer scaffolds, etc.) in relation to frozen tissue specimens, in relation to formalin-fixed and parafin-embedded (FFPE) specimens, etc.), organs, whole organisms, cell suspensions, single cells, organelles, within organelles, viruses, microorganisms, and other natural structures. Location characterization can additionally or alternatively be performed in relation to non-naturally occurring structures, such as microwells, microarrays, scaffolds, and other non-naturally occurring structures. For instance, the invention(s) can have in situ and/or in vivo applications, with infusion of functionalized particles into a sample (e.g., into a cell, into a tissue, into an organ, etc.). Examples of infusion can include one or more of: injection, electroporation, use of vectors (e.g., viral vectors), and other infusion methods.

In relation to location characterization in multiple dimensions, particles of the composition(s) described can be implemented in monolayer form (e.g., with manufacturing processes to apply composition units in monolayer or near-monolayer form, with systems that apply magnetic or other forces to form particle monolayers, etc.), with sample (e.g., tissue, cells) positioned adjacent the monolayer for subsequent processing and mapping. Alternatively, particles of the composition(s) described can be infused into a sample/specimen (e.g., by magnetic force, by electroporation, by using vectors, etc.). Alternatively, particles of the composition(s) described can be coupled to a surface of a sample/specimen (e.g., by chemical binding, by magnetic binding, by other binding), in order to enable surface mapping. Alternatively, particles of the composition(s) described can be guided or otherwise retained in 3D structures (e.g., in grids, in non-grid structures), such as microwells, microarrays (e.g., with nucleic acids capturing particles), scaffolds (e.g., hydrogels), or other 3D structures. In a related application, physical or other forces can be used to define structures (e.g., close packed structures) for distributions of particles that interact with samples to enable mapping. Alternatively, in relation to location characterization in multiple dimensions, particles of composition(s) described can be randomly distributed in space.

The systems, methods, and devices provide improved applications in spatial transcriptomics. For instance, compositions, methods, and systems described can be used for mapping of targets in a sample over time, in order to understand disease pathology and progression (e.g., spread of targets and changes in expression over time).

The invention(s) confer(s) the benefit of providing non-naturally occurring compositions for facilitating capture of target biological material from a sample and mapping distributions of target biological material in space (e.g., two-dimensional [2D] space, three-dimensional [3D] space), while providing one or more identifiers of the target biological material and/or neighboring material. Such compositions can include materials that have been modified from their natural states (e.g., in terms of providing structural differences from natural compositions). Furthermore, the invention(s) relate to combinations of materials, where the combinations of materials are non-naturally occurring (e.g., there is no naturally occurring counterpart to the compositions described and claimed).

As such, applications of the invention(s) can include improved performance of spatial multi-omics (e.g., spatial transcriptomics, spatial genomics, etc.), using novel functionalized particles for target detection and mapping.

The invention(s) also confer(s) the benefit of providing mechanisms for efficient capture and labeling of target material (e.g., DNA, RNA, miRNA, proteins, small molecules, single analytes, multianalytes, etc.) in order to enable analyses for mapping distributions of target material. For nucleic acid targets, capture probes of compositions described can include complementary molecules to the nucleic acid targets. For protein targets or small molecule targets, capture probes of the compositions described can include antibodies or aptamers conjugated with specific nucleic acid sequences for detection.

The invention(s) also confer(s) the benefit of enabling mapping of targets in multiple dimensions (e.g., 2D, 3D), where mapping can be performed in relation to whole tissue structures, tissue pieces (e.g., tissue slices as in histology, in relation to biopsied tissues, in relation to tissue blocks in relation to seeded scaffolds, etc.), droplets (e.g., of an emulsion), organs, whole organisms, cell suspensions, single cells, organelles, within organelles, viruses, microorganisms, and other natural structures. Mapping can additionally or alternatively be performed in relation to non-naturally occurring structures, such as microwells, microarrays, scaffolds, and other non-naturally occurring structures.

By incorporating molecular structures configured for interactions with neighboring objects (e.g., other units of the composition), the invention(s) enable capturing of targets, and subsequent decoding of spatial relationships between particles associated with the captured targets, which can then be used to determine locations of the targets in space (e.g., in situ, with respect to other naturally and non-naturally occurring structures, etc.)

In relation to mapping in multiple dimensions, particles of the composition(s) described can be implemented in monolayer form (e.g., with systems that apply magnetic or other forces to form particle monolayers), with sample (e.g., tissue, cells) positioned adjacent the monolayer for subsequent processing and mapping. Monolayers can be stacked between samples, in order to enable 3D mapping. Alternatively, particles of the composition(s) described can be infused into a sample/specimen (e.g., by magnetic force, by electroporation, by using vectors, etc.). Alternatively, particles of the composition(s) described can be coupled to a surface of a sample/specimen (e.g., by chemical binding, by magnetic binding, by other binding), in order to enable surface mapping. Alternatively, particles of the composition(s) described can be guided or otherwise retained in 3D structures (e.g., in grids, in non-grid structures), such as microwells, microarrays (e.g., with nucleic acids capturing particles), scaffolds, or other 3D structures. In a related application, physical or other forces can be used to define structures (e.g., close packed structures) for distributions of particles that interact with samples to enable mapping.

Alternatively, in relation to mapping in multiple dimensions, particles of the composition(s) described can be randomly distributed in space.

The invention(s) also confer(s) the benefit of enabling applications in spatial transcriptomics. For instance, compositions, methods, and systems described can be used for mapping of targets in a sample over time, in order to understand disease pathology and progression (e.g., spread of targets and changes in expression over time).

Additionally or alternatively, the systems, devices, or methods described can confer any other suitable benefit.

2. Systems

As shown in FIG. 1A, a system 100 for characterizing locations of target analytes of a sample, can include: a substrate no; and a distribution of functionalized particles 120 coupled to the substrate, wherein each of the distribution of functionalized particles includes: a body 130 reversibly coupled to the substrate, and one or more molecules 140 coupled to the body, the one or more molecules 140 including at least: a capture segment 141, a barcode segment 142, and optionally, a first cleavable linker 143 coupled to the body. The system 100 functions to interact with a sample and/or target analytes of a sample, in order to enable characterization of the location(s) of the target analytes in space.

In embodiments, the target analytes can include one or more of: nucleic acid material (e.g., DNA, RNA, miRNA, etc.), protein material, amino acid material, other small molecules, other single analytes, other multi-analytes, and/ or other suitable target material of a sample. In embodiments, the sample can include whole tissue structures, tissue portions (e.g., histological tissue slices, formalin-fixed paraffin-embedded (FFPE) tissue, frozen tissue, biopsied tissues, fresh frozen plasma, seeded natural scaffolds, seeded synthetic scaffolds, etc.), organs, whole organisms, organoids, cell suspensions (e.g., frozen cell suspensions that are separated prior to processing with the system, cell suspensions retained in a medium/hydrogel medium, etc.), nuclei suspension, single cells, organelles, sub-organelle structures, intra-organelle components, viruses, microorganisms, and other samples.

In some non-limiting examples, sample material from which targets can be captured can include one or more of: nervous system biological material, cardiovascular system biological material, integumentary system biological material, skeletal system biological material, muscular system biological material, respiratory system biological material, digestive system biological material, endocrine system biological material, urinary system biological material, and reproductive system biological material. Cellular material can be associated with normal and diseased states, including one or more of: cancer cells, circulating tumor cells, metastatic cells, benign cells, or any combination thereof. In embodiments, the sample can include solid/contiguous tissue material obtained from a subject.

Details of the system 100 and use thereof are described in further detail in the following sections.

2.1 System—Substrate

The substrate 110 functions to provide one or more surfaces onto which the distribution of functionalized particles 120 is patterned or otherwise deposited (as described below). The substrate 110 thus functions to support the distribution of functionalized particles 120 in a reliable manner during sample handling and processing. The substrate 110 can additionally or alternatively function to support mechanisms for controlled interactions with the distribution of functionalized particles (e.g., with respect to controllable binding and release mechanisms, etc.). The substrate no can additionally or alternatively function to facilitate detection of optical signals generated from interactions between the distribution of functionalized particles 120 and captured target analytes of the sample, by having suitable optical characteristics for transmission of light signals to an optical signal sensing apparatus. However, in variations, the substrate no can be processed to release functionalized particles, which are processed to characterize the distribution of functionalized particles away from the substrate 110. The substrate no can additionally or alternatively function to enable transmission of heat to a sample interacting with the system 100 during use, in order to promote interactions between the target analytes and the distribution of functionalized particles 120 at the substrate no. Additionally or alternatively, the substrate no can have other suitable functionality.

In one embodiment, the substrate no is composed of glass/silica (e.g., a borosilicate glass), which offers desired properties for manufacturing (e.g., in relation to surface functionalization, in relation to processing, in relation to separation of composition units, etc.), thermal characteristics (e.g., in terms of thermal conductivity, electrical characteristics (e.g., in terms of supporting charge, in terms of electrical conductivity, etc.), optical characteristics (e.g., providing mechanisms for optical recognition, characterized by one or more optical features encoding a set of nucleic acid bases, the set of nucleic acid bases identifiable upon detection of the one or more optical features, etc.), magnetic properties (e.g., in relation to providing or supporting magnetic fields for manipulation of sample components and/or aspects of the distribution of functionalized particles 120), biocompatibility characteristics, and/or other suitable characteristics. Alternatively, the substrate no can include, or be composed of one or more of: plastic/polymer materials (e.g., acrylic, cyclic olefin polymer, polycarbonate, poly(methyl methacrylate) (PMMA), cyclo olefin polymer (COP), polystyrene, polypropylene, polyethylene terephthalate glycolmodified (PEGT), etc.); ternary compositions (e.g., indium tin oxide); and/or other suitable materials.

In variations, the substrate 110 has a characteristic roughness less than or equal to 1 micrometer (e.g., 0.8 micrometer), but can alternatively have another suitable roughness. For instance, variations of the substrate 110 can have a desired roughness (e.g., greater than 1 micrometer) to provide a desired texture or serve other suitable functionality.

Additionally or alternatively, the substrate no can be flexible (e.g., composed of a flexible material) in order to enable applications involving flexible application to a sample surface (e.g., wrapping around a tissue body, etc.).

Figure 1B:
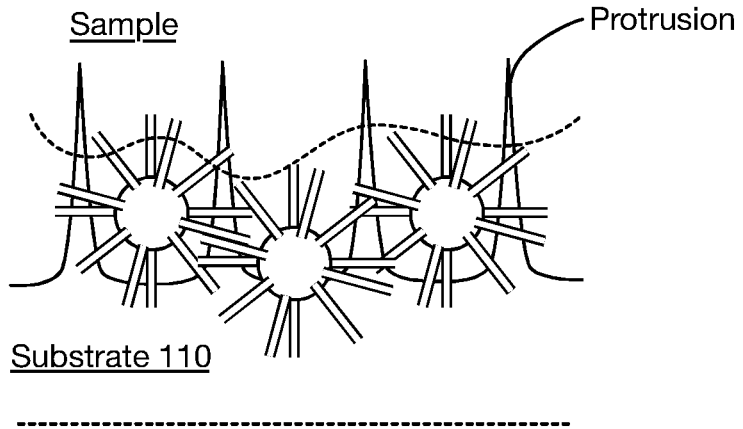
FIG. 1B depicts variations of substrates of a system for characterizing locations of target analytes in space.
Figure 1B:
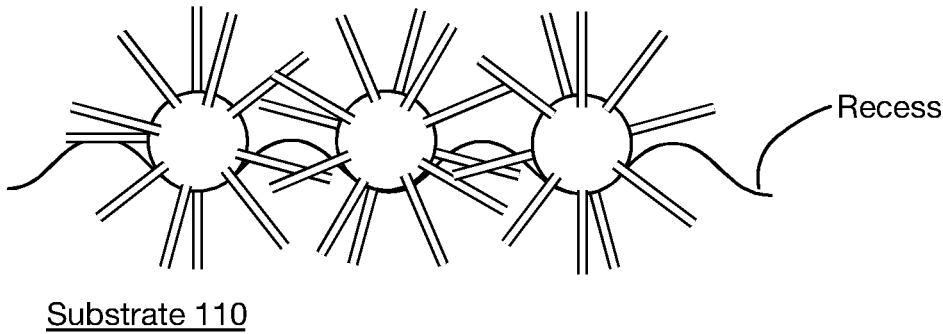

In some variations, as shown in FIG. 1B, the substrate no (and/or functionalized particle surfaces) can include a set of protrusions establishing an interface between the sample and the distribution of functionalized particles during use. As such, during operation, protrusions of the substrate no can be configured to extend into the sample (e.g., into tissue) to promote desired interactions between deeper portions of the sample and the distribution of functionalized particles at the substrate no. In a related variation, the protrusions can be hollow (e.g., as in microneedles), to aid transmission of fluid material to the sample (e.g., for sample processing) and/or to promote target analyte capture.

Additionally or alternatively, as shown in FIG. 1B, the substrate no can include a set of recesses configured to receive or otherwise support the distribution of functionalized particles 120, for instance, for positioning of the distribution of functionalized particles 120 at the substrate 110 in a desired configuration (e.g., patterned manner, with desired density, in a monodisperse manner, in monolayer, etc.).

Additionally or alternatively, the substrate 110 can include or be positioned adjacent to a set of fiducials, where the set of fiducials can provide observable markings for manufacturing (e.g., in relation to scribing/sawing of the substrate to separate units). Additionally or alternatively, the set of fiducials can define addressable locations of the system 100/distribution of functionalized particles for characterizing locations of target analytes of the sample captured using the system 100.

Additionally or alternatively, the substrate 110 can be optically recognizable (e.g., such that the substrate can be observed with optical apparatus to provide a signal). In variations, the substrate can be characterized by one or more optical features encoding a set of nucleic acid bases, the set of nucleic acid bases identifiable upon detection of the one or more optical features.

2.2 System—Functionalized Particles

As shown in FIG. 1A, the system 100 further includes a distribution of functionalized particles 120 coupled to the substrate, in order to enable analyses for characterizing locations of target material in space. The distribution of functionalized particles 120 functions to capture target analytes from the sample, and to provide functionality for decoding aspects of the target analytes and/or locations of each target analyte unit in space, upon sequencing. each functionalized particles 120 includes a body 130 (e.g., a body reversibly coupled to the substrate 110), and one or more molecules 140 coupled to the body, the one or more molecules 140 including at least: a capture segment 141, a barcode segment 142, and a first cleavable linker 143 coupled to the body.

In embodiments, the distribution of functionalized particles 120 is arranged at the substrate no (e.g., using a templating process, using another suitable process) with a circular footprint; however, in other variations the distribution of functionalized particles 120 can be arranged with other suitable morphology (e.g., an ellipsoidal footprint, a rectangular footprint, a polygonal footprint, an amorphous footprint, etc.). In one such example, the distribution of functionalized particles 120 is arranged with a square footprint having a corner notch for orientation purposes. In still other variations, the distribution of functionalized particles 120 can be patterned onto the substrate no in an arrangement corresponding to the sample(s) being processed using the system 100. For instance, in some variations, the distribution of functionalized particles 120 can be patterned in a manner corresponding to a characteristic sample shape (e.g., tissue biopsy shape), characteristic sample structural features (e.g., tissue fiber orientations), characteristic sample container shape (e.g., tube shape, well shape, etc.), and/or other suitable feature.

In variations, a characteristic dimension (e.g., diameter, width, length, etc.) of the arrangement in bulk of the distribution of functionalized particles 120 can range from 1 to 10 mm (or alternatively, greater than 10 mm), and in specific examples, the characteristic dimension of the distribution of functionalized particles 120 can range from 2 to 4 mm (e.g., in diameter for a circular footprint). In examples, larger tiles can be used to accommodate larger tissue samples, in order to generate spatial maps of larger tissue samples. However, the distribution of functionalized particles 120 can alternatively have another suitable characteristic dimension.

Furthermore, a substrate can have more than one distribution of functionalized particles 120, as shown in FIG. 7B, where the distributions (e.g., 120a through 120i shown in FIG. 7B) can be arranged in an array or otherwise arranged. In variations, the distributions can be arranged in a 2×2 array, a 3×3 array, or any other suitable array (ordered or non-ordered) on a substrate. Arrays of distributions of particles can be used to accommodate larger tissue samples, in order to generate spatial maps of larger tissue samples. As such, methods using arrayed distributions can include applying a sample (e.g., tissue sample), to an array of distributions of functionalized particles, and processing the sample according to embodiments, variations, and examples of method steps described. Furthermore, one or more distributions of functionalized particles at a substrate can include differences in barcode sequences (e.g., each unit of the array can have a different barcode sequence), which can be used for selective amplification and sequencing of different regions of a sample applied to the array. In one example, a region of interest associated with a first unit of the array can be selectively amplified and sequenced using the unique barcode sequence of the unit. If results from the region of interest are promising or otherwise satisfy a condition (e.g., quality condition) that warrants additional investigation, then the method can include selective amplification and sequencing of other regions of the sample, using the unique barcode sequences of the other units.

In some cases, the distribution of functionalized particles 120 is arranged at the substrate no with a high degree of density (e.g., hexagonal close packing, rectangular close packing, near-close packing, etc.). In specific examples, the distribution of functionalized particles is characterized by a high level of occupancy at the surface of the substrate 110. In relation to close packing of particles (e.g., random close packing), the packing density at the substrate can be from 55% to 74%, such that the empty or dead space between particles is from 26% to 45%. As such, the configuration of the distribution of functionalized particles achieves minimal dead space, as permitted by physics.

However, the distribution of functionalized particles can be characterized by another suitable percent occupancy. In some cases, the distribution is also monodisperse (e.g., uniformly distributed and with particles of substantially uniform size, with a critical distance between particles below a threshold); however, the distribution can alternatively be non-monodisperse/random. As such, application of the distribution of functionalized particles can be random or guided by morphology of the substrate (e.g., with meshes, with wells, with protrusions, with recesses, with textures, etc.).

In some cases, the distribution of functionalized particles is arranged at the substrate no in a monolayer (e.g., without stacking); however, in variations, the distribution of functionalized particles 120 can be arranged at the substrate no with a different degree of density (e.g., non-packed) and/or in non-monolayer format. In one such variation, the distribution of functionalized particles can be arranged in one or more sub-arrays (e.g., patterned for a specific application of use). In examples, the sub-arrays can include a different sub-arrays functionalized for different target analytes, different forms of target analytes (e.g., such as for different epitopes), control regions, or other suitable regions. Additionally or alternatively, multiple distributions can be arranged at a single substrate (e.g., an array or matrix of distributions of functionalized particles, arranged in discrete zones at the substrate).

The distribution of functionalized particles 120 can be coupled to the substrate no using a layer 112 to which particles can adhere (e.g., in a reversible manner, in a permanent manner). In variations, the distribution of functionalized particles 120 can be coupled to the substrate no by way of the layer 112 (shown in FIG. 1A) in a coupled operation mode, and separated from the substrate no in a separated operation mode. The adhesion or pull-off force for separation can range from 200 to 500 nano-Newtons; however, in other variations, the adhesion or pull-off force can be less than 200 nano-Newtons or greater than 500 nano-Newtons.

In variations, separation can be achieved using a detergent that separates the distribution of functionalized particles 120 from the layer 112 and/or substrate no directly. As such, by coupling of the distribution of functionalized particles can be provided by at least one of a hydrophobic interaction and a hydrophilic interaction that is reversible by addition of a detergent separation. Additionally or alternatively, separation can be achieved with linkers (e.g., cleavable linkers) coupling the functionalized particles to the layer or substrate (e.g., by a chemical modification at the substrate), where the linkers are configured to be cleave in response to one or more of: a thermal cleavage mechanism, a pH shift, a photocleaving mechanism, a chemical cleaving mechanism, an enzymatic cleaving mechanism (e.g., as in molecular scissors), separation based upon changes in charge (e.g., as in an electrostatic interaction), or another suitable cleaving/separation mechanism.

Functionalized particles can have an adherence of a threshold force level (e.g., 100 nano-Newtons, 200 nano-Newtons, greater than 200 nano-Newtons, etc.) prior to cleavage.

The layer 112 can be composed of a rubber (e.g., thermoplastic rubber) and/or other suitable polymer, and in specific examples, includes one or more of: an isoprene-based material, a styrene-based material, a propylene-based material, an ethylene-based material, a nylon-based material, and other suitable rubber/polymer materials. However, in other variations, the layer 112 can alternatively be composed of another suitable material.

The layer 112 can be hydrophobic, or can alternatively have a suitable degree of hydrophilicity, in relation to fabrication processes (e.g., using a spraying process, using a vapor deposition process, using a spin-coating process, using a printing process, etc.) and coupling of the distribution of functionalized particles 120 to the layer. The layer 112 can further be composed of a thermoplastic material, or can alternatively be composed of a thermosetting material. The layer 112 can be processed in liquid form (e.g., with suitable solvents) and applied to the substrate no using one or more processes (described in further detail below); however, the layer 112 can additionally or alternatively be applied to the substrate no in another suitable manner (e.g., as a pre-generated film, using a printing process, using a patterning process, etc.). For instance, in some examples, the layer 112 can be applied to the substrate no with a pattern or texture that promotes preferential coupling of the distribution of functionalized particles 120 to the layer 112 with a desired pattern and/or density (e.g., by using hydrophobic characteristics, hydrophilic characteristics, chemical bond characteristics, etc.).

Additionally or alternatively, adherence can be supported and/or reversed using magnetic forces. For instance, as described above, functionalized particles can have or be composed of magnetic materials, and manipulated (e.g., retained in position or separated from a substrate) by application, reversal, and/or removal of magnetic forces.

In relation to manufacturing processes described in further detail below, multiple distributions of functionalized particles can be arranged at a bulk substrate, and separated from each other to create units of the system 100. Additional details of manufacturing are described in more detail below.

Furthermore, during use, and in an application of use involving spatial characterization of target analytes in 3D, stacks of substrates with distributions of functionalized particles can be implemented (e.g., with layering of samples/slices of tissue and units of the system 100). As such, the system 100 can include additional substrates with distributions of functionalized particles (e.g., a second substrate with a second distribution of functionalized particles, a third substrate with a third distribution of functionalized particles, etc.), with layering of sample and reconstruction of 3D volumes by stitching data derived from implementation of the various substrates.

Embodiments, variations, and examples of the distribution of functionalized particles can additionally or alternatively include particle compositions described in U.S. application Ser. No. 17/376,396 filed on 15 Jul. 2021, which is herein incorporated in its entirety by this reference. Such functionalized particles for determining nearest neighbor interactions can thus be provided with substrates or other natural/synthetic structures in order to characterize locations of target analytes in space.

2.2.1 Functionalized Particles

Each body 130 of the distribution of functionalized particles 120 functions to provide a surface to which the one or more molecules 140 can be coupled, in order to provide functionalization for target analyte capture, sample processing, and subsequent location characterization operations.

In relation to morphology, the body 130 can have the form of a microsphere. Alternatively, the body 130 can have the form of a non-spherical (e.g., ellipsoidal, prismatic, polyhedral, amorphous, nanotube, etc.) body, where a cross section taken through the body 110 is non-circular. However, the body 130 can alternatively have another suitable form. For instance, in variations, the bodies 130 can be quantum dots responsive to excitation by different types of energy (e.g., wavelength ranges of electromagnetic energy for various applications.

In relation to dimensions, the body 130 can have a diameter (or characteristic width) on the order of nanometers to micrometers in dimension, where particle size determines the resolution of target analyte location characterization. Dimensional characteristics of the body 130 correspond to scales appropriate for characterization of target analyte locations for various structures (e.g., cells, tissues, and organs, sub-cellular structures, whole organisms, other components, etc.). In variations, the body 130 can have a diameter that is sub-micron up through 10 micrometers; however, alternative variations of the body 130 can have other suitable dimensions (e.g., less than sub-micron, greater than 10 micrometers in diameter). In specific examples, the dimensions of the bodies can be from 3-5 micrometers. In relation to body dimensions below 6 micrometers, tissue processing steps (e.g., permeabilization steps) can be optimized to prevent leakage of targets toward particles not proximal to their respective originating positions at the sample. Alternatively, the sample may not be permeabilized, such that the method involves positioning a non-permeabilized tissue sample at the substrate, thereby avoiding target diffusion away from origination positions in the sample, and preventing background noise (i.e., producing high SNR values) during spatial mapping. As such, use of particles having smaller dimensions can still be used to achieve accurate mapping without producing background noise attributed to target leakage or other noise sources.

The body 130 can have suitable density characteristics (e.g., with density less than, greater than, or equal to various process liquids associated with processing and characterization operations); porosity (e.g., with pore sizes of 100-2000 Angstroms, etc.); thermal properties (e.g., with respect to melting temperatures, with respect to conductivity, with respect to temperature sensitivity/responsiveness, etc.); physical properties (e.g., with respect to swelling characteristics, with respect to leaching characteristics, with respect to hydrophilicity, with respect to crosslinking, etc.); surface properties (e.g., binding sites for linker molecules, functional chemical groups, charge, etc.); magnetic properties (e.g., magnetic properties, paramagnetic properties, for instance by incorporation of magnetic nanoparticles, etc.); fluorescence properties (e.g., non-fluorescence so as to not interfere with optical-based detection assays, fluorescent/optical feature properties, such as fluorescence-embedded labels, encoding nucleic acid bases identifiable upon detection of the optical features, etc.); buoyant properties (e.g., in order to arrange particles at a surface due to buoyancy, and applying the sample to the buoyant distribution at the surface to which the buoyant particles migrate); mechanical properties (e.g., hardness, rigidity, elastic behavior, viscoelastic behavior, fatigue resistance, fracture resistance, shear strength, compressive strength, tensile strength, rheological behavior, etc.); solubility (e.g., dissolvable in a solvent, etc.); pH sensitivity; and/or other suitable properties, embodiments, variations, and examples of which are described in U.S. application Ser. No. 17/376,396 filed on 15 Jul. 2021, which is herein incorporated in its entirety by this reference.

In relation to composition, the body 130 can be composed of one or more of: polymers (e.g. polystyrene, polystyrene-divinylbenzene, polymethylmethacrylate (PMMA), etc.), hydrogels, silica, silicon, non-porous glass, porous glass, coated glass, agarose, acrylamide, polyacrylamide, iron, steel, or ceramic materials and/or a combination of one or more suitable materials. Different regions of the body 130 can be composed of different materials (e.g., a core region can be composed of a first material and a shell region can be composed of a second material). Additionally or alternatively, the body can be treated or otherwise compatible with phosphoramidite chemistry for synthesis of oligonucleotides onto the body 130. In specific examples, synthesis can be performed by: synthesizing constant sequences in a single column, followed by deprotection, then distribution of bodies across four columns, each configured to add one of an A, T, G, or C phosphoramidite to the bodies. Then, the bodies can be pooled, mixed well, and redistributed across the four columns for addition of an A, T, G, or C phosphoramidite to the bodies. As such, the barcode sequence added to each bead is randomized, but all oligonucleotides on each bead will have the same sequence. Synthesis can implement use of exonucleases to remove or otherwise avoid undesired levels of truncated oligonucleotides of the functionalized particles.

In some embodiments the body 130 can include multiple regions either as multiple shell regions, or in other configurations such as amorphous or ordered spatial arrangements. In still further examples, the body 130 can include or take the form of a polymeric/molecular body (e.g., DNA nanoball, dendrimer, etc.), where, in applications, the dendrimers can be reduced in size to a "functional monomer" (i.e., as a smallest functional molecular assembly unit).

Each body has one or more molecules 140 coupled thereto and structured to provide functionality as described below. The occupancy of molecules at the surface of each particle can be configured to prevent crowding, prevent self-hybridization, and/or enable access of target analytes and/or enzymes as required during processing. In embodiments, the one or more molecules 140 include at least: a capture segment 141, a barcode segment 142, and optionally a first cleavable linker 143 coupled to the body 130 (however, non-cleavable linkers can also be used for functionalization and providing attachment points for oligonucleotides). As described below, the one or more molecules 140 can include or omit regions based upon application of use. The density of the one or more molecules can be at least 10 times more than the amount of target analyte intended for capture from the sample(s), or otherwise configured with another suitable density in other applications of use.

The capture segment 141 functions to capture the target analyte of interest from the sample. The capture segment 141 is preferably positioned at a terminal end of a respective molecule in order to promote interactions with target analytes of the sample; however, the capture segment 141 can alternatively be otherwise positioned along a molecule. In variations, analytes captured by the capture probe 141 can include: nucleic acids (e.g., DNA, mRNA, miRNA etc.), oligonucleotides with polyT for mRNA capture, oligonucleotides without polyT, with a oligonucleotide with polyT attached to other types of molecules (e.g., antibodies, proteins, peptides, chemicals, etc.), antibodies, aptamers, and/or other suitable capture segments.

In one variation, the capture segment 141 can be configured for target mRNA binding (e.g., dT, dTVN for capturing polyA mRNAs). In downstream applications, captured target mRNAs can be processed (e.g., using reverse transcription to append the capture segments 141 with captured mRNAs with cDNA, followed by amplification of synthesized cDNA, followed by sequencing for target readout, etc.). In alternative variations, the capture segment 141 can include functionality for capture of one or more of: DNAs, other RNAs (e.g., miRNA), proteins (e.g., antibodies, using TotalSeq™ molecules), small molecules, single analytes, multianalytes, etc.), and/or other target material (e.g., to generate combinatorial libraries).

The capture segment 141 can additionally or alternatively be a gene-specific sequence to capture a set of specific genes or targets. The analytes can be modified to have a polyA tail (e.g. oligonucleotide-conjugated antibody, aptamer, peptide, etc.), or analyte-specific sequence, such that they can be captured by the capture probe via DNA complementarity. The capture segment 141 can also be a sequence with complementarity to a sequence on other sets of beads.

Further embodiments, variations, and examples of the capture segment 141 can be structured as described in U.S. application Ser. No. 17/376,396 filed on 15 Jul. 2021, as incorporated by reference above.

The barcode segment 142 functions to enable identification of the functionalized particle with which it is associated, upon sequencing of the barcode segment 142. In some variations, the barcode segment 142 and/or other variations of the barcode segment 142 can function to enable identification of the substrate no, entire distribution of functionalized particles 120 associated with the substrate no, and/or position of a functionalized particle (and thus captured target analyte), upon sequencing. As such, readout of the barcode segment 142 can facilitate characterization of the distribution of target analytes at the substrate no and/or other aspects of the substrate no and distribution of functionalized particles 120.

The barcode segment 142 is preferably configured to be unique to each functionalized particle. Furthermore, the barcode segments 142 are configured to have diversity such that each functionalized particle or group of functionalized particles associated with the substrate no can be uniquely identified. In particular, the diversity of the bead barcode library can be at least 10-fold more than the number of functionalized particles deposited at the substrate, such that almost every functionalized particle has unique barcode on the substrate. Alternatively, the barcode segment 142 can be characterized in terms of diversity in another suitable manner. In embodiments, the barcode segment 142 can have from 5-50 bases in order to provide a sufficient number of unique sequences for a desired number of particles in solution for a given process (i.e., such that each particle can be uniquely identified); however, in alternative variations, the barcode segment 142 can have other suitable numbers of bases (e.g., less than 5 bases, more than 50 bases). Additionally or alternatively, the barcode segment 142 can have a number of bases designed to occupy a percentage (e.g., 10%, 20%, 30%, etc.) of the length of a unit of a respective molecule of a functionalized particle.

Furthermore, in some variations, a percentage of functionalized particles can have known barcode sequences and can be spiked in amongst the distribution of functionalized particles to serve quality control functions for downstream sequencing operations (e.g., in situ sequencing operations).

In use, decoding of the barcode/associated location can be performed using an optical approach (e.g., sequencing-by-synthesis with or without reversible terminators, in-situ sequencing that is ligation based, hybridization based, rolling circle amplification-based, fluorescence in situ hybridization-based, etc.), using a nearest-neighbor approach with a next generation sequencing readout (as described in the applications incorporated by reference), using morphology of the functionalized particles (e.g., using a pattern etched on the particle or other uniquely identifiable particle morphological feature, each feature associated with one barcode), using a combination of fluorescent colors emitted from the functionalized particle (e.g., each combination of fluorescent colors corresponding to a barcode), and/or using another suitable method.

In examples, decoding of the barcode/associated location can include performing a sequencing by ligation (SOLiD) operation to decode nucleic acid labels (e.g., with sequencing primer sites, with UP primer sites, etc.) and positions of associate labels on functionalized particles at the substrate. Sequencing/decoding can be performed using a microfluidic device having a flow cell by which units the system 100 are processed for decoding prior to packing and delivery (e.g., in series, in parallel). The microfluidic device can thus control flow of materials for interactions with units of the substrate, in coordination with an imaging system having a field of view encompassing the substrate(s) configured to capture images from which sequences of the barcodes can be determined in relation to substrate positions.

The optional first cleavable linker 143 is coupled to the body 130 and functions to provide a mechanism by which molecules coupled to the body 130 can be controllably released from the body 130 (e.g., post-interaction with target analytes). The first cleavable linker 143 can also extend units of the one or more molecules 140 out into space, thereby enabling interactions of the one or more molecules 140 with target analytes of the sample.

In embodiments, the optional first cleavable linker 143 is configured for selectable attachment (e.g., with functional groups specific to specific chemistries) and/or activatable cleavage, to enable controlled release of the one or more molecules 140 from the body 130, and/or controllable release of material derived from captured target analytes for downstream processing. In variations, activatable cleavage or separation in another manner can be achieved with linker regions configured to be cleave in response to one or more of: a thermal cleavage mechanism, a pH shift, a photocleaving mechanism, an enzymatic cleaving mechanism (e.g., as in molecular scissors), separation based upon changes in charge, or another suitable cleaving mechanism.

In composition, the optional first cleavable linker 143 is preferably composed of a polymer (e.g., non-nucleic acid polymer), and in a specific example, the first cleavable linker 143 can be composed of polyethylene glycol (PEG) or another suitable polymer. However, the first cleavable linker 143 can be composed of another suitable material (e.g., natural material, synthetic material).

In structure, the optional first cleavable linker 143 can have a linear structure that extends units of the one or more molecules 140 into space. Alternatively, the first cleavable linker 143 can have a branched or otherwise non-linear structure (e.g., dendrimer segment, other branched segment). For instance, in variations in which the first cleavable linker 143 is configured to control spacing/density of molecules coupled to the body 130, the first cleavable linker 143 can have a branched structure that reduces density and/or controls spacing/orientation of molecules coupled to the body 130. Additionally or alternatively, the length and/or structure of the optional first cleavable linker 143 can be configured to prevent steric hindrance of any enzyme or material that would interact with the oligonucleotide molecules during use.

In relation to properties, the first cleavable linker 143 can be configured with a desired charge and/or other characteristic (e.g., level of hydrophilicity, level of hydrophobicity, etc.) that prevents undesired interactions between molecules (e.g., tangling, clumping, undesired structures, etc.). As such, the first cleavable linker 143 can be configured to extend molecules of the one or more molecules 140 into space (e.g., perpendicular from a surface of the body 130); however, the first cleavable linker 143 can be configured to extend from the body 130 in another suitable manner.

In variations, units of the one or more molecules can omit or include additional segments as needed. For instance, one or more of the one or more molecules 140 can include segments configured for amplification reactions (e.g., PCR handles, etc.). Additionally or alternatively, one or more of the one or more molecules 140 can include fluorescence-embedded labels. Additionally or alternatively, one or more of the one or more of the one or more molecules can include segments configured to simplify library preparation steps or sequencing processes of specific sequencing platforms. In more detail, molecules of the one or more molecules can include adapter segments (e.g., associated with P5/P7 adapters for Illumina™ platforms), index sequences associated with adapters, and/or other sequences. Additionally or alternatively, additional segments can be added during sample processing (e.g., during reverse transcription, etc.). Units of the one or more molecules 140 can additionally or alternatively include other sequences (e.g., for other fragmentation/sequencing/processing platforms). In embodiments, the molecules can be produced/synthesized by at least one of split pool synthesis (e.g., chemically, with an oligo synthesizer, etc.), enzymatic synthesis (e.g., with ligation and polymerase extension), by emulsion PCR, by template-free synthesis (e.g., using terminal transferase, etc.), and/or by other suitable methods, as described in more detail below.

Some embodiments, variations, and examples of molecule segments are further described in U.S. application Ser. No. 17/376,396 filed on 15 Jul. 2021, which is incorporated by reference above.

Moreover, an embodiment of a composition for mapping of molecules includes a body and a set of molecules coupled to the body and structured for functionalization of the composition.

In embodiments, the set of molecules can include a first subset of molecules structured for target analyte capture, where a unit of the first subset can include one or more of: a first anchor segment, a first particle identification segment (P), a unique molecule identifier (M), and a capture probe. In embodiments, the set of molecules can include a second subset of molecules structured for interactions with one or more neighboring objects (e.g., other units of the composition), where a unit of the second subset can include one or more of: a linker region, a second anchor segment, a second particle identification segment (P), and an active segment for interactions with a neighboring object. In applications, the composition can be provided as a set of particles (e.g., in solution), wherein each of the set of particles is coupled to (e.g., coated with) molecules for various assays associated with mapping of locations of target molecules of a biological sample.

The composition can be configured for processes and reactions associated with target capture and neighboring object detection, including one or more of: reverse transcription reactions (RT-reactions) for cDNA synthesis associated with target capture, amplification reactions (e.g., PCR) for amplification of cDNA, high throughput sequencing, ligation, hybridization, polymerase extension, and other suitable reactions. Such reactions can be performed in relation to systems (described in further detail below) including one or more of: natural structures (e.g., organelles, cells, tissues, organs, natural scaffolds, etc.), synthetic structures (e.g., arrays, synthetic scaffolds, microwells, etc.), and/or random dispersions of sample materials.

In some non-limiting examples, sample material from which targets can be captured can include one or more of: nervous system biological material, cardiovascular system biological material, integumentary system biological material, skeletal system biological material, muscular system biological material, respiratory system biological material, digestive system biological material, endocrine system biological material, urinary system biological material, and reproductive system biological material. Cellular material can be associated with normal and diseased states, including one or more of: cancer cells, circulating tumor cells, metastatic cells, benign cells, or any combination thereof. In embodiments, the sample can include solid/contiguous tissue material obtained from a subject.

2.3 System—Support Structure and Use

As shown in FIG. 2, the invention(s) can further include a support structure 200, which functions to support one or more units of the system 100 and to facilitate usage of the system 100 by a sample-processing entity. In embodiments, the support structure 200 can retain one or more units of the system 100 in position, facilitate contacting of units of the system 100 by a tissue sample or other sample, and enable release of the one or more units of the system 100 from the support structure 200 for further processing, post-interactions with sample material.

Figure 2A:
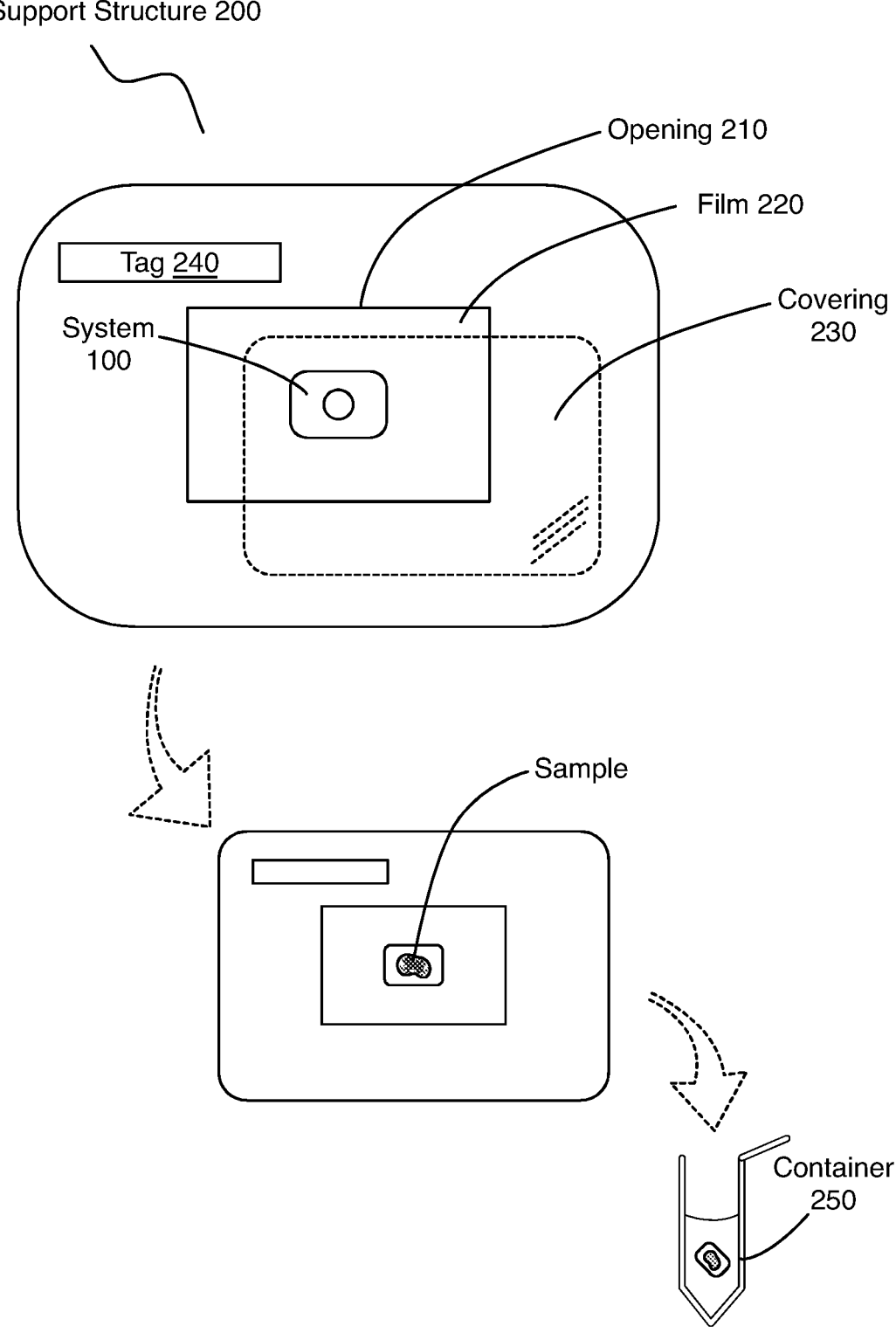
FIG. 2A depicts a schematic of an embodiment of a support structure for a system for characterizing locations of target analytes in space.
Figure 2B:
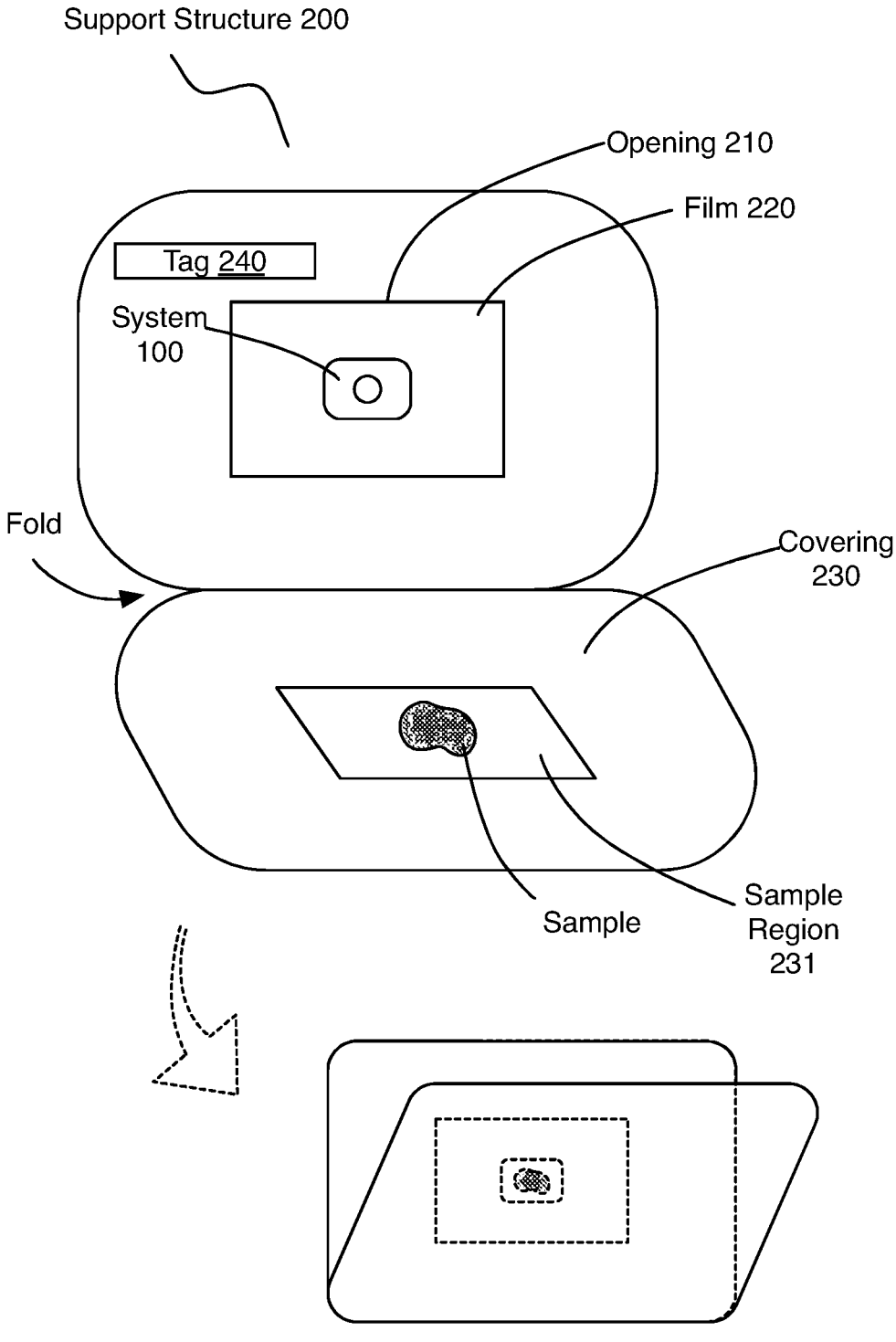
FIG. 2B depicts a schematic of a variation of a support structure for a system for characterizing locations of target analytes in space.

In embodiments, as shown in FIGS. 2A and 2B, the support structure 200 includes: an opening 210, and a flexible film 220 coupled to the support structure about the opening 210 at a first surface of the support structure, and supporting one or more units of the system 100 (e.g., substrate no with functionalized particles 120, array of substrates with functionalized particles, etc.) within the opening 210. In variations, the support structure 200 can further include one or more of: a protective covering 230 opposing the flexible film 220 at the opening 210, and a tag 240 encoding information associated with the system 100/substrate 110.

Details of embodiments, variations, and examples of the support structure 200 and related structural components are further described as follows:

In embodiments, the support structure 200 is composed of a material that provides protection from environments associated with transportation and/or use of the system 100. As such, the support structure 200 can function to provide one or more of: impact resistance (e.g., to protect fragile portions of the system 100), flame-proofing/resistance; sealing (e.g., as in a hermetic seal, in order to prevent intrusion of moisture prior to use, in order to prevent intrusion of gases prior to use, etc.); optical properties (e.g., with respect to shielding from electromagnetic energy, with respect to allowing transmission of light for enabling optical detection or visual observation through the support structure 200, etc.); electrical properties (e.g., with respect to shielding from electric fields, etc.); and/or other suitable properties. In examples, the support structure 200 can be composed of a polymer material, a fibrous material, a foam, or another suitable material.

In morphology, the support structure 200 can have a broad surface, where the broad surface is rectangular in morphology; however, in other variations, the support structure 200 can have another suitable defined morphology (e.g., circular morphology, ellipsoidal morphology, polygonal morphology, amorphous morphology, etc.). In examples, the support structure 200 can have a characteristic length from 1-15 centimeters, a characteristic width from 1-15 centimeters, and a characteristic thickness from 0.5-5 millimeters; however, the support structure 200 can alternatively have other suitable dimensions.

In variations, the support structure 200 can include features configured to facilitate handling by an operator. For instance, the support structure 200 can include surface regions with high-friction (e.g., to facilitate gripping by a human or robotic operator), markings (e.g., to provide indications of orientation, to guide proper usage of the support structure 200 in relation to various operation modes, etc.), and/or other features.

The opening 210 functions to enable an operator to interact with the system 100 according to operation modes described below, when the system 100 is supported by the support structure 200. In particular, the opening 210 can allow the operator to transmit heat to a sample (e.g., through the flexible film 220 described in more detail below) and/or to displace the system 100 from the support structure 200 (e.g., by application of a mechanical force to the flexible film 220 described in more detail below). The opening 210 can be rectangular in morphology; however, in other variations, the opening can have another suitable defined morphology (e.g., circular morphology, ellipsoidal morphology, polygonal morphology, amorphous morphology, etc.). In examples, the opening 210 can have a characteristic length from 0.2-10 centimeters, a characteristic width from 0.2-10 centimeters, and a characteristic depth from 0.5-5 millimeters; however, the support structure 200 can alternatively have other suitable dimensions.

The support structure 200 can include a single opening 210. Alternatively, the support structure 200 can include a set of openings (e.g., arranged as an array, arranged in another suitable manner), where each opening of the set of openings is configured to support one or more units of the system 100.

The flexible film 220 functions to support the system 100 within the opening 210 (or multiple openings), and to enable operation modes described in more detail below. Properties of the flexible film 220 can allow an operator to transmit heat to a sample (e.g., through the flexible film 220 and/or substrate no) and/or to displace the system 100 from the support structure 200 (e.g., by application of a mechanical force to the flexible film 220).

In embodiments, the flexible film 220 is retained in position about the opening 210 (e.g., coupled to a broad surface of the support structure 210, retained between layers of the support structure 210, etc.). The flexible film 220 can be retained without any slack or under tension. Preferably, the flexible film 220 is retained in a manner such that application of force or heat to the flexible film 220, as intended during use during operation modes described below, does not compromise coupling of the flexible film 220 to the support structure 200 or compromise its functionality. Alternatively, the flexible film 220 can be retained in position about the opening 210 in another suitable manner.

The flexible film 220 is preferably composed of a material processed with: suitable mechanical properties (e.g., in relation to tear strength, in relation to strain behavior, in relation to allowing plastic deformation for displacement of the system 100 from the support structure 200, in relation to allowing elastic deformation for displacement of the system 100 from the support structure 200, etc.), optical properties (e.g., degree of transparency to allow observation of a unit of the system 100 coupled to the flexible film 220 during use), thermal properties (e.g., in relation to conductivity for transmission of heat to a sample through the flexible film 220 and substrate 110, in relation to melting temperature, etc.), surface and bulk properties (e.g., in relation to charge, in relation to degree of hydrophobicity, in relation to porosity, etc.), electrical properties, and/or other suitable properties. The flexible film 120 can have a thickness from 75 to 150 micrometers (or alternatively, another suitable thickness).

In embodiments, the flexible film 120 is a flexible polymer film composed of polyvinyl chloride (PVC), polyolefin, polyethylene, polyethylene terephthalate (PET), nylon, and/or another suitable polymer material. In variations, the flexible film 120 further includes an adhesive layer coupled thereto, in order to provide a mechanism for coupling with units of the system 100 in a non-permanent manner. In variations, the adhesive layer is composed of an acrylic adhesive; however variations of the adhesive layer can be composed of another suitable material. The adhesive layer can have an adhesive strength configured based upon size and mass characteristics of the system 100 and/or in relation to specified force required to displace a unit of the system 100 from the flexible film 120 during use. In a specific example, the flexible film 120 is a PVC dicing tape used during manufacturing of the substrate 110 (e.g., with respect to scribing and sawing of the substrate 110); however, in variations of the specific example, the flexible film 120 can be otherwise composed and configured.

For instance, as an alternative to mechanical breaking of adhesive bonds, the adhesive layer can be structured such that adhesive bonds are broken upon exposure to specific wavelength ranges of light (e.g., ultraviolet light, etc.), thermal stimulation (e.g., upon exposure to heat at certain temperature ranges), and/or another suitable mechanism.

The protective covering 230 functions to protect units of the system 100 supported by the support structure 200 (e.g., during transportation, during phases of use, etc.). In some embodiments the protective covering 230 is composed of the same material as the bulk material used for the support structure 200; however, the protective covering can alternatively be composed of another suitable material, embodiments, variations, and examples of which are described above.

The protective covering 230 can be an element separate from the bulk material of the support structure 200, such that the protective covering 230 can be provided with the support structure 200 (e.g., in relation to the kit/package described in more detail below), and removed from the support structure 200 during use. Alternatively, the protective covering 230 can be physically contiguous with the bulk material of the support structure 200 and/or transitionable between a covered mode (e.g., in which units of the system 100 are covered) and an uncovered mode (e.g., in which units of the system 100 are uncovered), where transition between modes can be enabled through folding, sliding, or another mechanism facilitated by structural relationships between the protective covering 230 and the bulk material of the support structure 200. In one such variation, as shown in FIG. 2B, the protective covering 230 can be folded over the opening 210 in the covered mode, and unfolded in the uncovered mode.

Sample retention and positioning for interactions with the system 100 can, however, be enabled by other suitable sample positioning structures.

Furthermore, in relation to operation modes described in more detail below, the protective covering 230 can include a sample region 231 configured to support or retain a sample, as shown in FIG. 2B, where the sample can be positioned at the sample region 231, and then transition of the protective covering 230 to the covered mode (e.g., through folding, through another mechanism) can position the sample into contact with the system 100 for sample processing in a consistent and reliable manner.

The tag 240 functions to encode information pertaining to one or more of the support structure 200, units of the system 100 supported by the support structure 200, reagents being provided with a kit including the support structure 200, the sample(s) being processed using the support structure 200, molecular barcode information (e.g., spatial locations associated with different molecular barcodes of distributions of functionalized particles 120, etc.). In variations, information encoded by the tag 240 can include one or more of: batch number (e.g., of the support structure 200, of a system 100 unit, of reagents), lot number (e.g., of the support structure 200, of a system 100 unit, of reagents), sample-identification information, patient or subject information associated with a sample, molecular barcode information (e.g., spatial locations associated with different molecular barcodes of distributions of functionalized particles 120, etc.), other spatial information (e.g., associated with a position of a system 100 unit at the support structure, associated with spatial locations of material at the system 100 unit), other molecular information, and/or other suitable information.

In embodiments, the tag 240 can be a computer-readable tag. In embodiments, the tag 240 can thus have the form of a barcode, a QR code, a code including characters (e.g., alpha-numeric characters, other characters, etc.), or another suitable code that is readable upon scanning (e.g., with an optical detection subsystem). Additionally or alternatively, the tag 240 can be a digitally-readable tag (e.g., decoded upon transmission of electrical signals).

Figure 3:
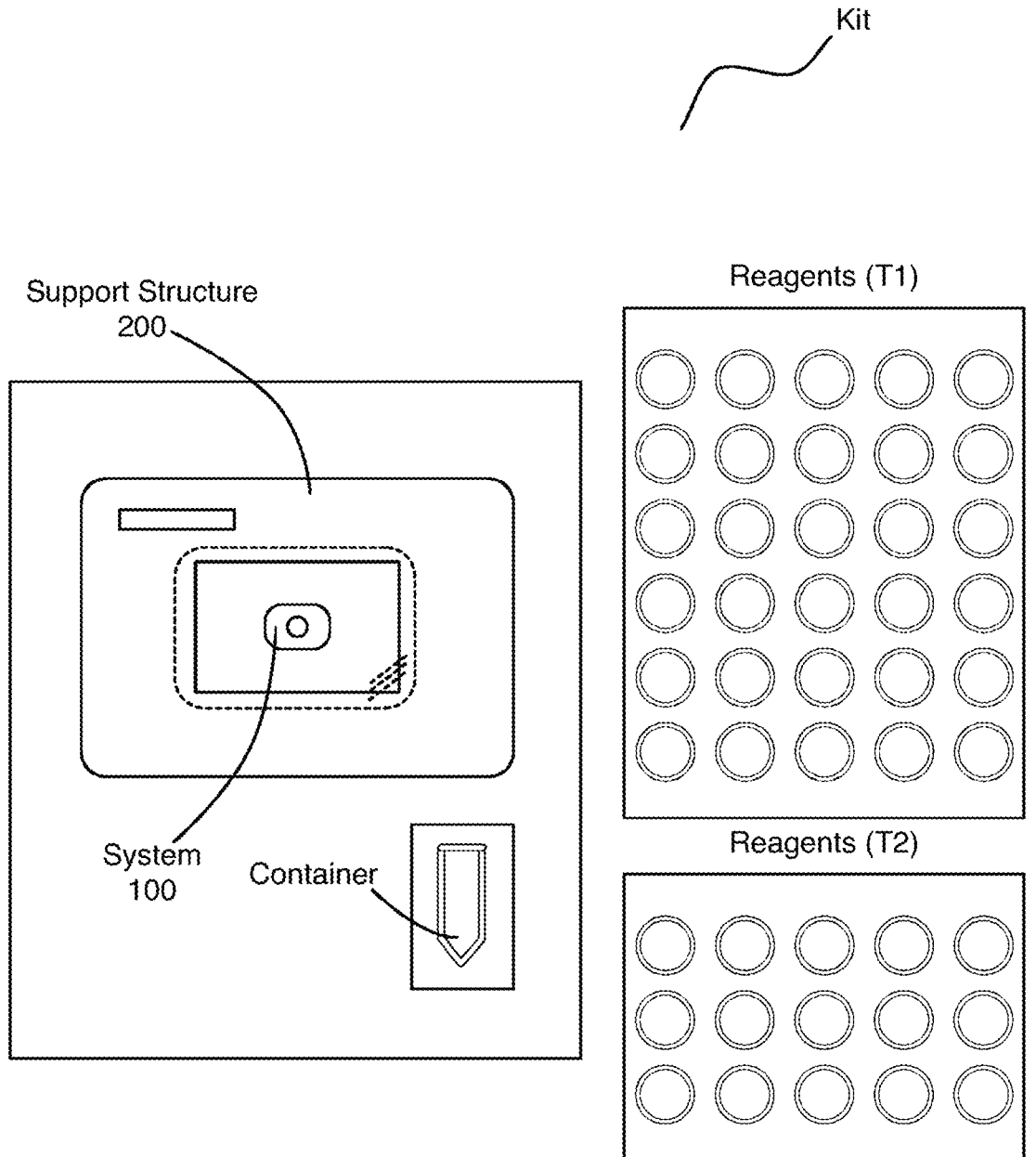
FIG. 3 depicts a schematic of a kit including elements for characterizing locations of target analytes in space.

In embodiments, the support structure 200 with one or more units of the system 100 can be provided as a kit (as shown in FIG. 3), where the support structure 200 is assembled (e.g., pre-packaged) with the one or more units of the system 100, including the substrate no with the distribution of functionalized particles 120. The kit can further include a process container 250 configured to receive one or more units of the system 100 (e.g., in relation to operation modes described below where the system 100 is displaced from the support structure into a container 250, such as a process container or collecting container).

Additionally or alternatively, the kit can further include one or more reagents for sample processing operations and/or for library preparation operations. One or more of the reagents can be provided in separate containers; additionally or alternatively, one or more of the reagents can be provided in container 250 (e.g., pre-packaged in container 250), in order to stabilize or store material captured at a unit of the system 100 (e.g. prior to transportation or other downstream processing operations).

In one variation, provided reagents can be designed for reception/storage of the system 100 at a first temperature (e.g., −20 C). In examples, the reagents can include one or more of: RNase inhibitor, superscript/reverse transcriptase buffer, reverse transcriptase enzyme, dNTPs, reverse transcription enzyme, template switching oligonucleotides, exosome isolation reagents, TC enzyme/buffer, superscript enzyme, amplification primers, PCR reagents (e.g., PCR buffer, PCR primer mix, PCR enzyme, etc.), proteinase K, exonuclease, cDNA amplification buffer, cDNA amplification primer mix(es), cDNA amplification amplification enzyme, TE, and/or other suitable reagents.

In another variation, provided reagents can be designed for reception/storage of the system 100 at a second temperature (e.g., 4 C, etc.). In examples, the reagents can include one or more of: functionalized particle washing buffer, TC enzyme/buffer, water (e.g., nuclease-free water), hybridization buffer, tissue clearing buffer, Tris buffer, sodium hydroxide, and/or other suitable reagents.

In another variation, provided reagents can be designed for reception/storage of the system 100 at a third temperature (e.g., room temperature, etc.). In examples, the reagents can include one or more of: functionalized particle washing buffer, TC enzyme/buffer, water (e.g., nuclease-free water), hybridization buffer, and/or other suitable reagents.

Additionally or alternatively, reagents can be configured for library preparation and/or other assays. In examples, library preparation materials can support hybridization (e.g., hybridization with whole genome sequencing primer sites, with universal primer (UP) sites, etc.), template switching reverse transcription (RT), sample and bead removal (e.g., within process container 250), exonuclease treatment or other methods of removing single stranded oligonucleotides from functionalized particles, denaturation steps (e.g., involving sodium hydroxide), second strand synthesis Reagents of the kit can be provided in a separate housing (e.g., container, box, etc.) from the support structure 200 and/or other system elements, examples of which are shown in FIG. 3. Additionally or alternatively, reagents of the kit can be provided in the same housing (e.g., container, box, etc.). Additionally or alternatively, the kit can include open receptacles (e.g., for optional or custom reagents), or can otherwise omit reagent provision.

Additionally or alternatively, the kit can include training substrates (e.g., substrates with or without functionalized particles, and/or with or without decoding of functionalized particle positions at the substrate), which can be used by new users to practice application of a sample to the substrate and/or to practice other aspects of using the kit.

2.3.1 Support Structure—Example Operation and Variations

During use, the support structure 200 can provide a set of operation modes for sample processing (e.g., with respect to protecting aspects of the system 100 during shipping/handling/processing, with respect promoting contact between units of the system 100 and samples during processing, with respect to enabling release of units of the system 100 from the support structure 200 for downstream processing, etc.).

Figure 4A:
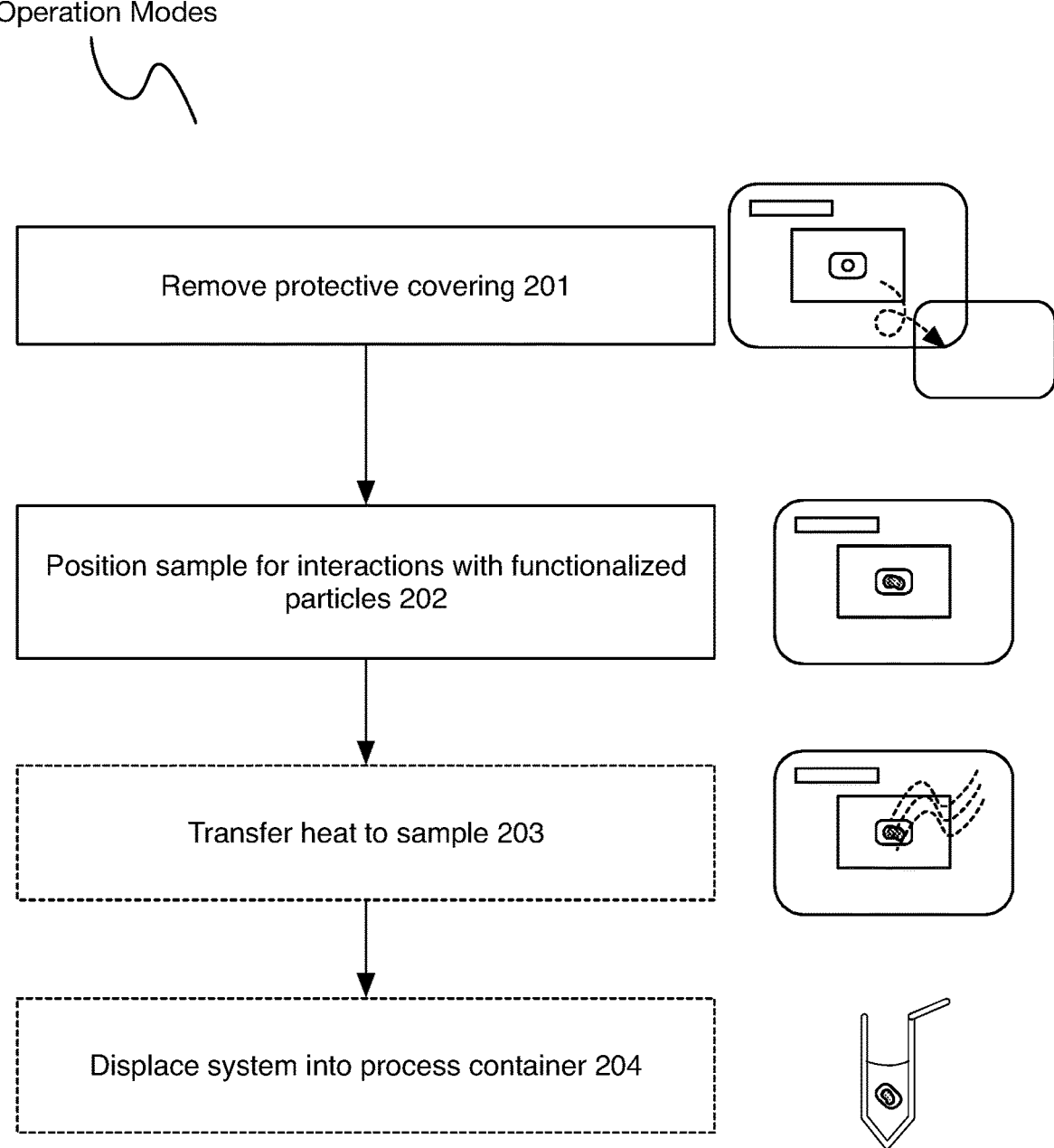
FIG. 4A depicts a flowchart of an example workflow of a system for characterizing locations of target analytes in space.

In variations, as shown in FIG. 4A, the set of operation modes can include a first operation mode 201 in which the protective covering 230 is removed from the support structure 200 or otherwise positioned away from the substrate 110; and a second operation mode 202 in which a sample is positioned in contact with the substrate no and the distribution of functionalized particles 120. The set of operation modes can further include a third operation mode 203 in which heat is transferred from the substrate no to the sample (e.g., in variations in which the sample is frozen, in variations in which the sample is paraffin-embedded, etc.); and a fourth operation mode in which the flexible film 220 is deformed, thereby displacing the substrate no, with or without the sample, from the support structure 200 and into a process container 250. Additionally or alternatively, additional operation modes can include facilitating removal of functionalized particles from the substrate no, within the process container 250 (e.g., by aspiration and delivery of liquid within the process container 250 to dislodge functionalized particles from the substrate no after they have interacted with the sample).

As described above, the first operation mode 201 and the second operation mode 202 can be associated with covered and uncovered modes provided by the protective covering 230, where the protective covering 230 can receive the sample, and transition to the covered mode (e.g., by folding), in order to position the sample into contact with the distribution of functionalized particles 120 at the substrate no. Operation modes 201 and 202 can be enabled by variations of the support structure 200 in another suitable manner (an example of which is described in relation to variation of the support structure 200b below).

In relation to operation mode 203, heat can be transferred from the substrate no to the sample through the flexible film 220. In a first example, an operator can position a warm object (e.g., finger, heating element, etc.) against the flexible film 220 opposite the system 100, and heat from the warm object can be transmitted to the sample (e.g., to melt the sample). In another example, a platform (e.g., automated platform) can transmit heat to the sample with a heat source (e.g., plate heater, convective heater, etc.) in thermal communication with the sample (e.g., through the flexible film, through the support structure, through the substrate, etc.). In particular, in relation to operation modes described, at least one of the flexible film 220, the substrate no, and the support structure 100 has a thermal conductivity of greater than a thermal conductivity threshold (e.g., 0.05 W/mK), providing a thermal transmission pathway to the sample during operation.

In relation to operation mode 204, the flexible film 220 is deformed, to displace the substrate 110 from the support structure 200 and into a process container 250 for transportation, storage and/or further processing (e.g., sequencing, etc.). In one variation, an operator can apply a force to the flexible film 220 (e.g., backside of the flexible film 200), to displace the substrate 110 from an adhesive layer coupled to the flexible film 220. In another variation, a robotic apparatus can apply a force (e.g., using a tip or other extremity) to the flexible film 220 (e.g., backside of the flexible film 200), to displace the substrate 110 from an adhesive layer coupled to the flexible film 220. In alternative variations, operation mode 204 can omit implementation of a mechanical force, and instead application of light within a specified wavelength range (e.g., UV light) and/or application of heat (e.g., at a specified temperature range) can promote separation of the substrate 110 from the film 220.

Figure 4B:
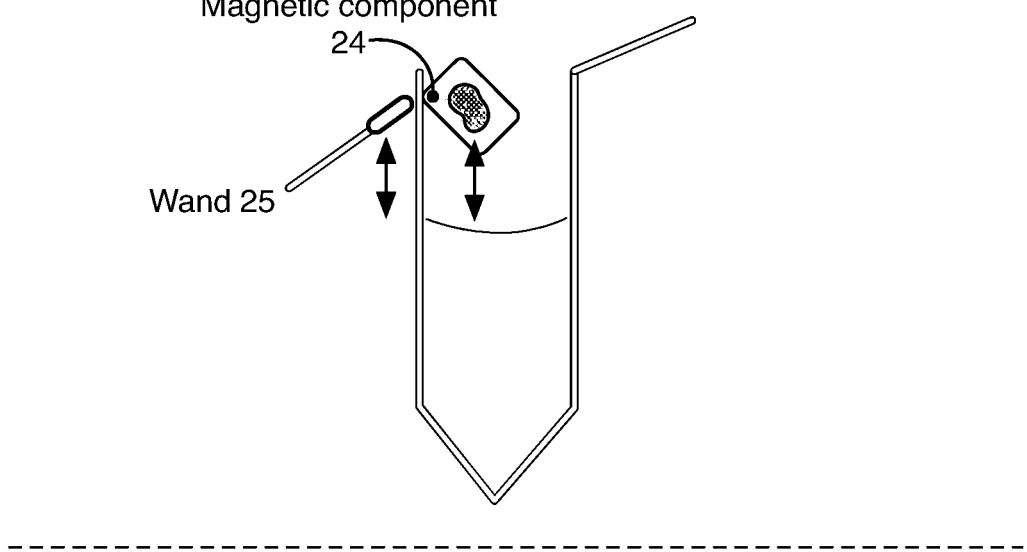
FIG. 4B depicts schematics of example workflow steps related to steps shown in FIG. 4A.
Figure 4B:
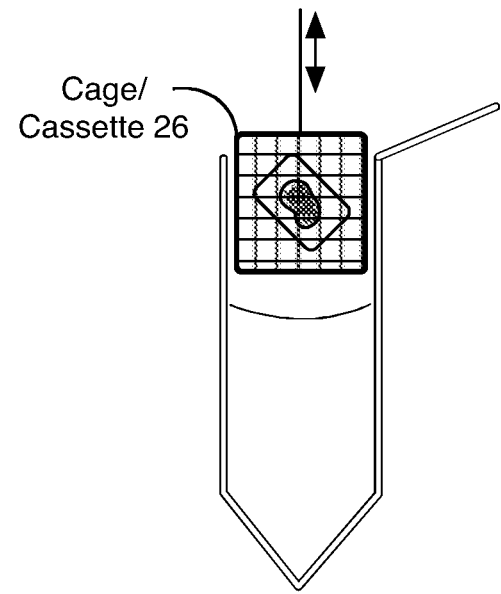

Additionally or alternatively, in relation to operation mode 204, the system can include a magnetic component 24 (e.g.) coupled to the substrate no, or to which the substrate no with the distribution of functionalized particles is transferred, prior to transfer of the substrate no into the process container, as shown in FIG. 4B (Top). Furthermore, the system 100 or other entity performing sample processing can apply magnetic forces (e.g., by actuating a magnetic wand/stylus 25) to the substrate no, in order to control motion of the substrate 110 into, out of, or within the process container 250 during sample processing steps.

Additionally or alternatively, in relation to operation mode 204, the system can include a cage/cassette 26 into which the substrate 110 with the distribution of functionalized particles is transferred in coordination with interacting the distribution of functionalized particles with the sample, where the cage/cassette can be manipulated more easily than the substrate, for controlling motion of the substrate 110 into, out of, or within the process container 250 during sample processing steps, as shown in FIG. 4B (Bottom).

In variations the film may not be flexible and can instead be rigid.

The invention(s) described can support further operation modes and/or include other elements. For instance, the invention(s) can include a flow cell configured to receive one or more units of the system 100 (e.g., post-interaction with samples, and post-displacement from a support structure), where the flow cell enables sequencing of target analytes, material derived from captured and processed target analytes, and/or other sample processing steps. Such a flow cell can thus include a fluid channel in communication with the distribution of functionalized particles at the substrate of a unit of the system, and enable optical detection of signals generated from captured and/or processed target analytes of the sample. Furthermore, the flow cell can enclose one or more units of the system for higher throughput and/or multiplexed operations.

Figure 5:
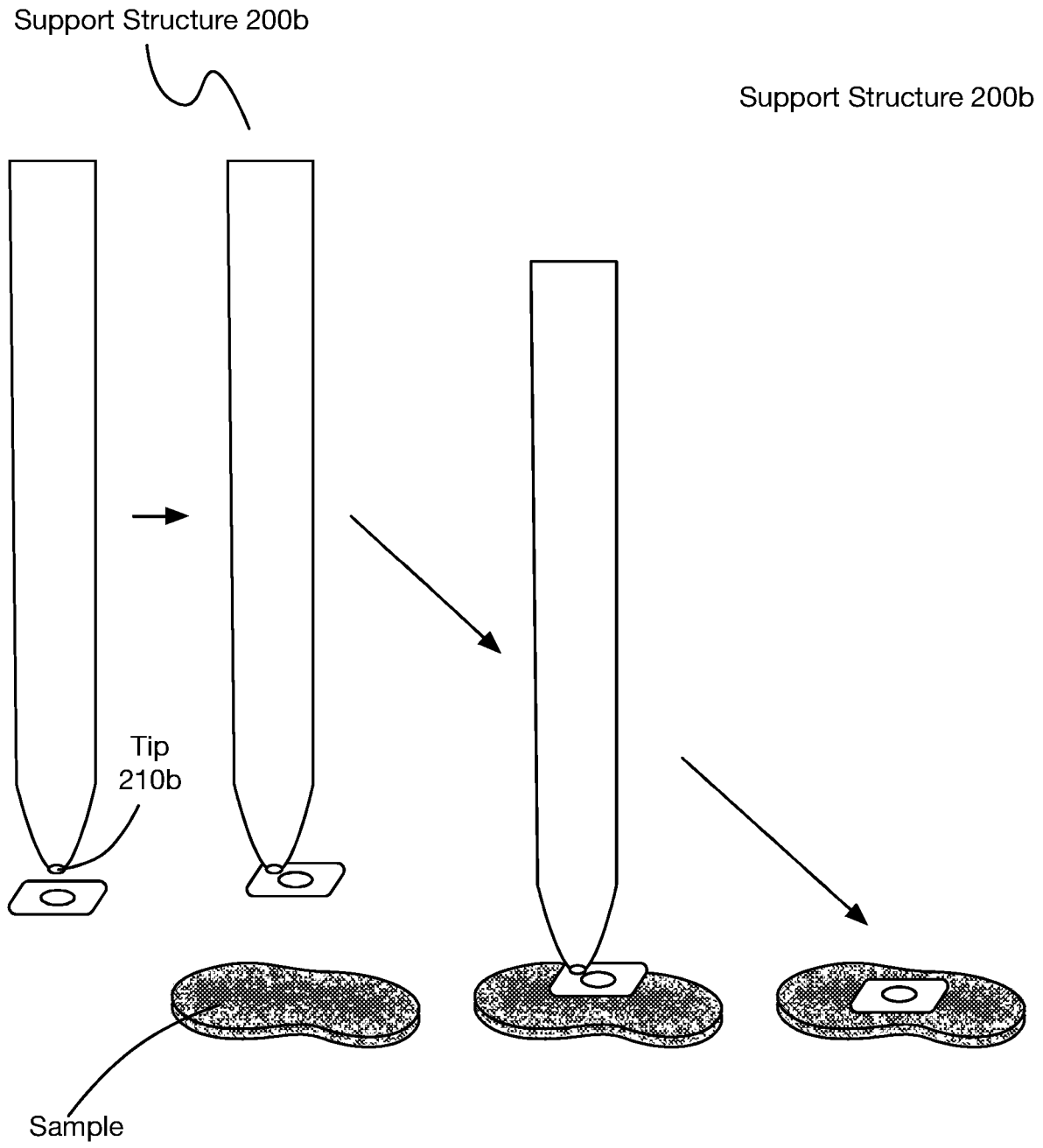
FIG. 5 depicts schematics of another variation of a support structure for a system for characterizing locations of target analytes in space and method of use.

Alternative Variation: In an alternative variation, as shown in FIG. 5, the support structure 200b can include a tip 210b supporting one or more units of the system 100, where, during use, the tip 210b can be positioned into contact with a sample, and the unit(s) of the system 100 can be displaced from the tip 210b to contact a specific portion of the sample. In examples, the unit(s) of the system 100 can be coupled to the tip 210b using a layer (e.g., adhesive layer), where contact with the sample provides a force that separates the system 100 from the layer to interact with the sample. Additionally or alternatively, the tip 210b and/or other portion of the support structure 200b can provide a controlled release mechanism using, for example, a plunger (e.g., mechanical plunger that displaces the system 100 from the tip 210b), magnetic forces (e.g., in which reversible polarity or removal of magnetic forces displaces the system 100 from the tip 210b), or other forces are used to separate the system 100 from the tip 210b.

Furthermore, the variation of the support structure 200b described can include multiple tips individually supporting units of the system 100, where the multiple tips can be synchronously controlled and/or individually controlled to displace respective units of the system 100 to promote sample interactions, target analyte capture, target analyte location characterization, and/or other aspects of sample processing.

In a specific application of use, a sample/tissue can still be integrated with a patient or other subject (e.g., not removed from the patient/subject), and in specific examples, the sample/tissue can include a skin sample (e.g., lesion) or other section of tissue made accessible (e.g., during a procedure for biopsy, during orthoscopy, during endoscopy, etc.), allowing sampling of the tissue without removal from the patient. For instance, in one specific use case, during removal of cancerous tissue, the support structure 200b can apply one or more system units to the neighboring tissue to help confirm if the cancerous tissue is completely removed. The support structure 200b can, however, be applied in other suitable manners.

Still other variations of the support structure can be otherwise configured with respect to promoting interactions with samples for target analyte capture, target analyte location characterization, and/or other aspects of sample processing. For instance, the system can include a sample positioning structure configured to retain the sample in position relative to the substrate.

3. Methods of Manufacturing

As shown in FIG. 6, a method 300 for manufacturing units of system embodiments described above includes: providing a substrate 310; and applying a distribution of functionalized particles to the substrate 320. Compositions of system components can be provided as described in the embodiments, variations, and examples covered in Section 2 above; however, compositions of system components can additionally or alternatively include other compositions.

Providing the substrate 310 can include providing a bulk substrate that can be separated into separate units (each having one or more distributions of functionalized particles). Separating the bulk substrate into separate units can implement fiducials that facilitate separation of the bulk substrate (e.g., manually, in an automated manner). In variations, the fiducial(s) can be coupled (e.g., etched into, applied with an adhesive, marked with an ink, chrome-marked, cut into, etc.) to the surface of the bulk substrate. Alternatively, the bulk substrate can be positioned adjacent to or retained in position adjacent to another substrate (e.g., sheet) having markings/fiducials during associated fabrication and separation operations. Additionally or alternatively, in relation to multiple distributions of functionalized particles on a substrate, each distribution can have associated fiducials for location identification purposes and/or other purposes Applying a distribution of functionalized particles to the substrate 320 can involve a coating and/or deposition process. In variations, step 320 can include coating or depositing layer 112 described above onto the surface of the substrate prior to coupling of the distribution of functionalized particles to the substrate. In one example, coating layer 112 onto the substrate involves spin-coating the layer 112 onto the substrate in one or more stages, each stage involving de-gassing material of the layer 112 (in liquid form, if solvents are present), and spin-coating the de-gassed material onto the substrate (e.g., with a final layer thickness from 0.05 to 2 millimeters). The coating process can include multiple coats, desired spin rates, dynamic dispensing of coating material, static dispensing of coating material, and/or suitable drying processes (e.g., between 35 and 60 C, with heating during centrifugation, etc.). Additionally or alternatively, the layer 112 can be deposited using an ultrasonic deposition process and/or other process (described further in relation to manufacturing methods below). The coating process can further produce a desired level of roughness and/or texture, as described above.

Then, applying the distribution of functionalized particles onto the substrate involves dispensing the distribution of functionalized particles, in solution, into openings of a template aligned in position with the substrate, followed by centrifugation (e.g., with heating at 40 C, at another suitable temperature), and drying. As such, the functionalized particles are applied randomly to the substrate within openings of the template. Additionally or alternatively, the distribution of functionalized particles can be spin-coated, printed, or applied in another suitable manner (described further in relation to manufacturing methods below). The openings of the template can be sized according to characteristic dimensions described above, and/or have desired shapes and morphologies as described above. The openings of the template can further be spaced to facilitate separation of units of the system in downstream manufacturing steps. In variations (shown in FIG. 7A), the openings can be circular (e.g., 1.5-5 millimeters in diameter), with center-to-center spacing ranging from 1.75 to 10 millimeters. In an alternative variation (shown in FIG. 7A), the openings can be square (3 millimeters by 3 millimeters) with a notch for orientation, and center-to-center spacing of 4.5-5 millimeters. However, the template can be otherwise configured.

Applying the distribution of functionalized particles can further include centrifuging the substrate (e.g., at a desired temperature) with the solution of functionalized particles, washing the substrate (e.g., to remove stacked/overlapping particles, to produce a monolayer of particles, etc.), implementation of reducing reagents, implementation of recovery reagents, and/or other suitable processing steps. In examples, washing the distribution of functionalized particles can include pelleting the functionalized particles and washing the pellet(s) with a wash buffer. Alternatively, in other examples, washing the distribution of functionalized particles can include performing washing of functionalized particles within a column (e.g., chromatographic column), using a wash buffer. However, washing can be performed in another suitable manner.

The distribution of functionalized particles can additionally or alternatively be applied using another suitable deposition, coating (e.g., ultrasonic coating), or printing process.

In embodiments, the method 300 can further include synthesizing the functionalized particles 315 (e.g., prior to application of the distribution of functionalized particles to the substrate), where synthesis can include functionalizing the particle bodies with linker molecules (e.g., as described above), and performing one or more synthesis operations (e.g., split pool synthesis with an oligonucleotide synthesizer, enzymatic synthesis with ligation and polymerase extension, emulsion PCR, etc.), to produce resultant functional molecules for target capture and identification, at each particle. Synthesis can further include agitation steps (e.g., agitation of functionalized particles) to promote control/consistency of synthesis. Synthesis can further implement use of exonucleases to remove truncated oligonucleotides that could interfere with capture or amplification efficiency, as well as accurate barcoding. In alternative variations, synthesis can include functionalization for protein or amino acid-associated assays (e.g., with etching of antibodies, with implementation of oligonucleotides with poly DA and antibody-specific barcodes, etc.), and/or other suitable processing steps.

Figure 8:
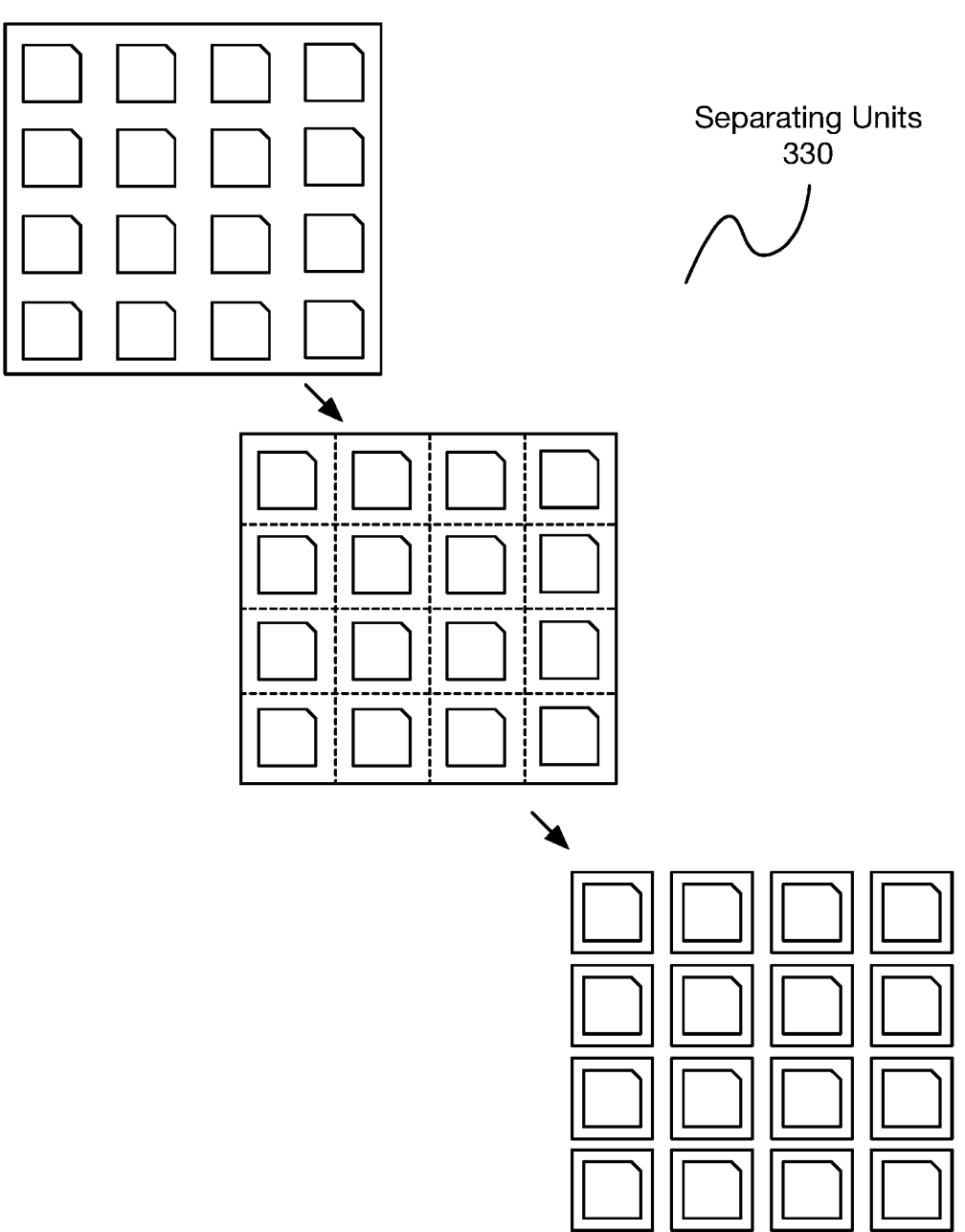
FIG. 8 depicts an example of separation of units of a system during manufacturing.

In some embodiments, the method 300 can further include separating units of the system from each other 330, which functions to enable scaling of manufacturing of system units in an efficient manner. In one variation, separating units can include scribing the bulk substrate between units of distributions of functionalized particles (e.g., using fiducials described above, using other alignment methods, etc.), and cleaving units from each other, according to the scribing pattern, as shown in FIG. 8. Additionally or alternatively, separating units can implement one or more of: etching, scoring, cutting (e.g., laser cutting), sawing, or another suitable separation method, with pick-up tools (e.g., vacuum tweezers, etc.) to relocate separated units for packaging. However, as described above, in relation to generating substrates with multiple units of distributions of particles, the bulk substrate can be separated in a manner that produces arrays of distributions of functionalized particle at each separated unit.

Additionally, the method 300 can further include generating documentation (e.g., text files, databases) of locations (e.g., in Cartesian coordinates, in cylindrical coordinates, in spherical coordinates, etc.) of functionalized particles and associated barcode sequences, as well as other information characterizing system, support structure, sample, and/or other aspects of the invention(s) described.

In specific examples, units of the system can be configured to fit within a collecting container (e.g., provided with kit described above), and be submerged or otherwise placed in contact with process fluids (e.g., for perfusion) in the collecting container. As such, in specific examples, separation of individual units of the bulk substrate can produce unit sizes having lengths from 3-10 millimeters and widths from 3-10 millimeters (e.g., with distances between units of 1 millimeter to 5 millimeters).

In variations, manufacturing and quality control (QC) operations associated with manufacturing and/or sequencing (e.g., with optimization to significantly reduce processing time) can include one or more of: assessing monolayer formation of functionalized particles (e.g., through image analysis, etc.); assessing smoothness or roughness of the coating of layer 112 (e.g., adhesive layer), such as through atomic force microscopy (AFM) or other suitable methods; detection and identification of spatial labels associated with target analytes by way of at least one of: in situ sequencing (e.g., ligation-based sequencing, hybridization-based sequencing, rolling circle amplification, other decoding operations, etc.) and detection of a spatial nucleic acid label associated with at least one of: a morphological feature of a functionalized particle and fluorescent compositions of particles during synthesis of the functionalized particle; operations to determine functionalized particle sensitivity; operations to improve focusing and image optimization associated with imaging subsystems used for sequencing (e.g., with magnification optimization to reduce number of images and/or image size); other operations to characterize capture efficiency (e.g., to produce greater than 90% recovery of oligonucleotides from functionalized particles, to produce greater than 85% recovery of oligonucleotides from functionalized particles, to produce other suitable capture efficiency rates, etc.); operations to improve the number of system units that can be processed in parallel within a flow cell (e.g., up to 100 system units per flow cell, greater than 100 system units per flow cell, etc.); operations to mitigate bubble formation-associated effects within a flow cell; operations associated with optimization of ligation, denaturing, and washing steps (e.g., during in-situ sequencing); and/or other suitable quality control operations.

4. Methods and Example Applications of Use

Figure 9A:
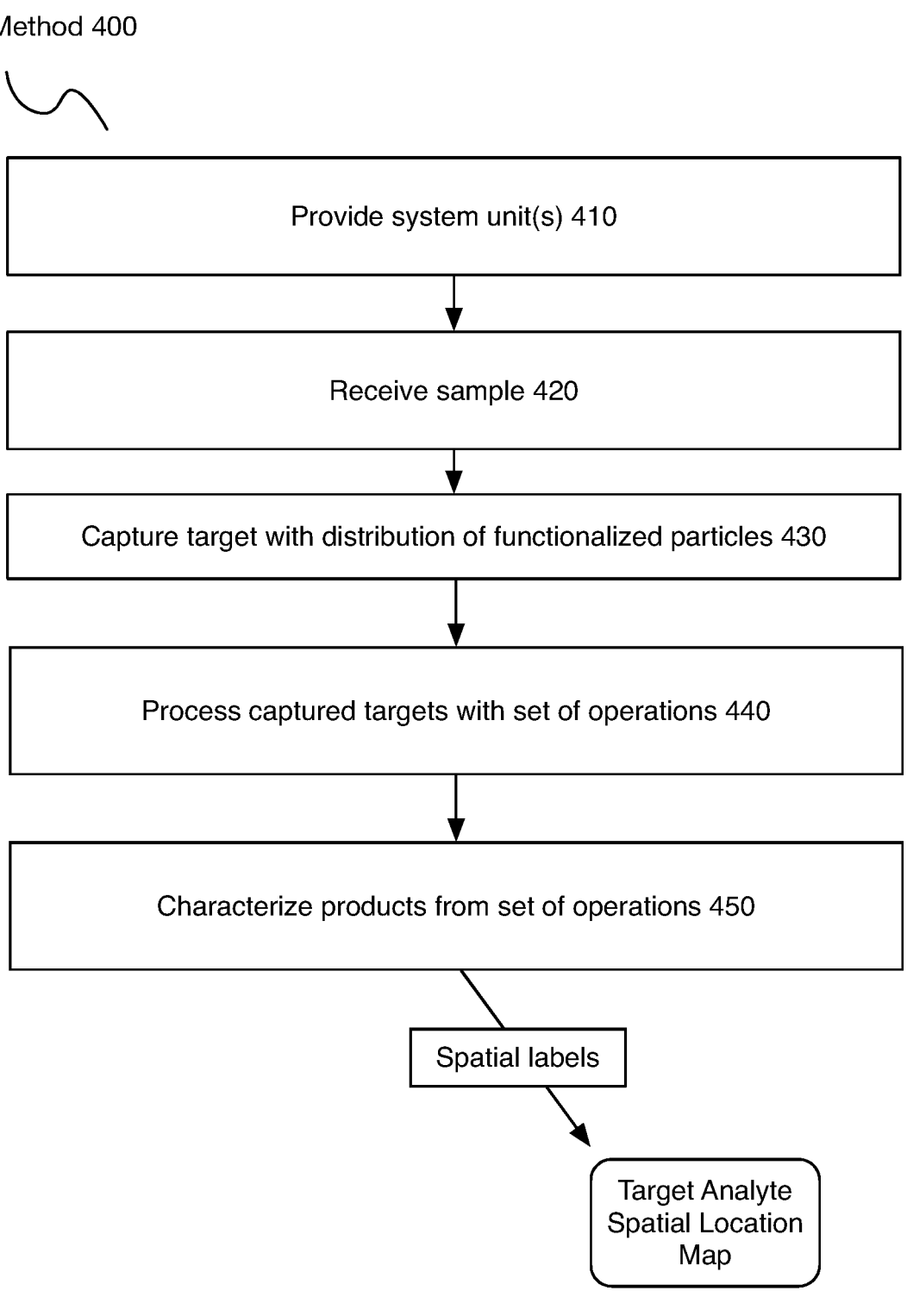
FIG. 9A depicts a flowchart of an embodiment of a method for characterizing locations of target analytes in space.

As shown in FIG. 9A, an embodiment of method 400 for characterizing locations of target analytes of a sample can include: providing a substrate having a distribution of functionalized particles coupled to the substrate, wherein each of the distribution of functionalized particles comprises a body, optionally a first cleavable linker coupling the body to the substrate, and one or more molecules coupled to the body, the one or more molecules comprising a capture segment, a barcode segment (e.g., stochastic barcode sequence described), and optionally a second cleavable linker coupled to the body 410; receiving the sample at the substrate 420; capturing target analytes of the sample by way of the distribution of functionalized particles at the substrate 430, upon promoting interactions between the distribution of targets of the sample and the distribution of functionalized particles; applying a set of reactions to the sample at the substrate, thereby processing captured target analytes of the sample with a set of operations 440; and characterizing products resulting from the set of operations 450 (e.g., obtaining a set of sequences of a population of molecules generated from the set of reactions, the set of sequences associated with the distribution of targets labeled using the stochastic barcode sequences of the distribution of functionalized particles) in order to return a set of positions of the distribution of targets. The method 400 functions to process one or more samples in order to characterize spatial locations of target analytes of the sample. The method 400 can additionally or alternatively provide other suitable functions (e.g., in relation to diagnostics for various pathologies, in relation to characterization of target analytes of a tissue, in relation to characterization of target analytes of distributions of single cells, etc.).

The method 400 can generate high-resolution spatial maps of targets of the sample(s), where, in examples, the method 400 can achieve resolutions of: greater than one target mapped per 500 um$^2$, greater than one target mapped per 400 um$^2$, greater than one target mapped per 300 um$^2$, greater than one target mapped per 200 um$^2$, greater than one target mapped per 150 um$^2$, greater than one target mapped per 100 um$^2$, greater than one target mapped per 50 um$^2$, greater than one target mapped per 40 um$^2$, greater than one target mapped per 30 um$^2$, greater than one target mapped per 20 um$^2$, greater than one target mapped per 10 um$^2$, or any intermediate number of targets mapped per unit area.

Mapping can be performing for each of a set of at least 2 targets, 3 targets, 4 targets, 5 targets, 6 targets, 7 targets, 8 targets, 9 targets, 10 targets, 11 targets, 12 targets, 13 targets, 14 targets, 15 targets, 16 targets, 17 targets, 18 targets, 19 targets, 20 targets, 25 targets, 30 targets, 40 targets, 50 targets, 100 targets, 1000 targets or any intermediate number of targets simultaneously, at resolutions described.

Generated maps can have an associated signal-to-noise ratio (SNR) of at least 100, 200, 300, 400, 500, 600, 700, 800, 900, 1000, 2000, 3000, 4000, 5000, 6000, 7000, 8000, 9000, 10000, 100000, or greater, where background noise is attributed to leakage of targets away from their original positions at the sample and toward functionalized particles that are positioned further away from the original positions at the sample. As such, SNR can be determined by calculating a ratio between a number of signal copies observed at "correct" positions and a number of background copies of targets present in "background" positions). In variations, determining the SNR can include: identifying one or a set of genes known to be expressed in regions (e.g., single cell types, single cell subtypes) of a sample (where such genes can be expressed at low level, such as less than 100 copies per particle, or at high level); quantifying expression of the one gene or the set of genes across the sample (e.g., according to method steps described below), determining a value of the signal from a measure of the expression of the one gene or the set of genes in regions that should express such gene(s), and determining a value of the noise from a measure of the expression of the one gene or the set of genes in regions that should not express such genes. The SNR can then be determined from the value of the signal divided by the value of the noise. In a specific example, for a mouse hippocampus sample, the SNR was determined using hippocalcin hpca) gene and transthyretin (ttr) gene, which are known to be expressed by certain hippocampus cell subtypes and not represented in other sample regions. Using hpca and ttr, the value of the noise was determined to be 0, indicating that hpca and ttr genes were not observed in regions that should not express hpca/ttr. As such, the SNR for the example sample type was shown to be infinite. Values of signal and noise can be determined from raw or normalized counts. Higher levels of noise can be attributed to anchoring of oligonucleotides onto glass substrates directly (e.g., without a particle layer intermediary), which can create different surface physical characteristics that promote target leakage and thus greater levels of background noise.

Generated maps can have an associated false positive rate less than a threshold number (e.g., a false positive percentage), where the false positive rate is determined from a percent (e.g., x %) of positive copies of targets observed beyond a threshold distance (e.g., y micrometers) away from where the positive copies ("signal") should actually originate from (e.g., originating positions of targets in the sample). In examples, the false positive rate can be less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5%, or less than another suitable percent. In examples, the threshold distance can be 15 micrometers, 14 micrometers, 13 micrometers, 12 micrometers, 11 micrometers, 10 micrometers, 9 micrometers, 8 micrometers, 7 micrometers, 6 micrometers, 5 micrometers, 4 micrometers, 3 micrometers, 2 micrometers, or another suitable threshold distance, where background noise is attributed to leakage of targets away from their original positions at the sample and toward functionalized particles that are positioned further away from the original positions at the sample. As such, the method 400 can include generating a spatial map of a distribution of targets of a tissue sample, wherein upon generating the spatial map by a set of processes, wherein the set of processes comprises: receiving the tissue sample at a substrate comprising a distribution of functionalized particles arranged in a random close packed configuration, each of the distribution of functionalized particles comprising a stochastic barcode sequence paired with a position on the substrate, applying a set of reactions to the tissue sample at the substrate, obtaining a set of sequences of a population of molecules generated from the set of reactions, the set of sequences associated with the distribution of targets labeled using the stochastic barcode sequences of the distribution of functionalized particles, returning a set of positions of the distribution of targets upon processing the set of sequences, identifying a gene with a known expression profile across regions of the tissue sample, and determining the false positive rate upon quantifying expression of the gene across the sample based upon the set of positions of the distribution of targets.

The method 400 can further achieve generation of spatial maps that have a resolution of less than a threshold distance between features (e.g., beads or other particle bodies, rods, protrusions, recesses, ridges, valleys, channels, wells, oligonucleotide spots, etc.) of a substrate for target capture/interactions. Embodiments, variations, and examples of spatial maps generated have a resolution of less than 50 picometers between features, less than 40 picometers between features, less than 30 picometers between features, less than 20 picometers between features, less than 10 picometers between features, less than 5 picometers between features, or less than 1 picometer between features In particular, in relation to platforms involving non-close-packed features (e.g., functionalized particles) for target capture and mapping, the invention(s) described achieve high resolution mapping with minimal (or non-existent noise, as described above), by having smaller functional unit areas and spatial unit areas for target capture. Furthermore, the systems described minimize the amount of empty or dead space between features for target capture, by close packing such features (e.g., in comparison to platforms where features are printed as spots that are spaced apart at the surface of a substrate, such as a glass slide). In examples, as shown in FIG. 1C, structural configurations of the features for target mapping, as in the inventions described, produce smaller capture areas per feature (and therefore higher resolution data), smaller spatial unit areas, smaller functional unit areas, less leakage of targets from the sample and therefore lower levels of background noise, and the ability to identify features (e.g., single cell subtypes) based upon a clustering analysis of spatial biomarkers, and without requiring deconvolution or other more involved computational approaches.

In embodiments, the target analytes characterized spatially according to the method 400 can include one or more of: nucleic acid material (e.g., DNA, RNA, miRNA, etc.), protein material, amino acid material, other small molecules, other single analytes, other multianalytes, and/or other suitable target material of a sample. In embodiments, the sample can include whole tissue structures, tissue portions (e.g., histological tissue slices, formalin-fixed paraffin-embedded (FFPE) tissue, frozen tissue, biopsied tissues, fresh frozen plasma, seeded natural scaffolds, seeded synthetic scaffolds, etc.), organs, whole organisms, organoids, cell suspensions (e.g., frozen cell suspensions that are separated prior to processing with the system, cell suspensions retained in a medium/hydrogel medium, etc.), nuclei suspension, single cells, organelles, sub-organelle structures, intra-organelle components, viruses, microorganisms, and other samples.

Samples can further be processed in other suitable manners prior to interactions with the system. For instance, sample processing can include one or more of: preserving sample material (e.g., through freezing, through fixing, through embedding, etc.), lysing sampling material, washing sample material, inducing cell/tissue swelling/expansion or shrinking (e.g., through hypertonic/hypotonic solutions), inducing cell/tissue gelling, clarifying cells/tissues (e.g., using lipid clarification), and/or other suitable processing steps.

In relation to frozen sample material, the method 400 can include freezing of sample material in a manner that lyses cell membranes and/or other sample structures. Alternatively, the method 400 can include freezing of sample material in a manner that preserves cell membranes and/or other sample structures. For instance, freezing in a preserving manner can implement one or more of: rapid freezing (e.g., in liquid nitrogen, in another freezing medium, at another freezing temperature); nucleating proteins, low molecular weight solutes, saccharides (e.g., glucose), or other compounds that draw water from cells (thereby reducing the amount of water turned to ice and reducing volumetric expansion during freezing); and/or other anti-freeze compounds, in order to implement the method without lysis or structural compromise (e.g., with respect to characterizing surface target analytes without disrupting original structures, etc.). Affecting the nature of sample freezing can further affect water volume and/or analyte concentration during sample processing.

In variations, captured target analytes can be processed and observed upon harvesting such target analytes and/or their derivatives after they have interacted with embodiments, variations, and examples of the system(s) and support structure(s) described above. Additionally or alternatively, the method can implement steps for observing and mapping locations of target analytes in space without harvesting of target analytes or derivatives from host tissues, cells, or other host material.

In some non-limiting examples, sample material from which targets can be captured and processed according to the method 400 can include natural tissue including one or more of: nervous system biological material (e.g., brain tissue, spinal cord tissue, nerve tissue, etc.), lymphatic system biological material (e.g., spleen tissue, lymph material, etc.), cardiovascular system biological material, integumentary system biological material, skeletal system biological material, muscular system biological material, respiratory system biological material, digestive system biological material, endocrine system biological material, urinary system biological material, and reproductive system biological material. Additionally or alternatively, sample material can include plant tissue material, fungal tissue material, or other material. Cellular material can be associated with normal and diseased states, including one or more of: cancer cells, circulating tumor cells, metastatic cells, benign cells, or any combination thereof. In embodiments, the sample can include solid/contiguous tissue material obtained from a subject.

In some non-limiting examples, sample material from which targets can be captured and processed according to the method 400 can include synthetic tissue including cell-seeded scaffolds or other composite material.

Receiving the sample at the substrate 420 can additionally or alternatively include implementing one or more structures for retention of the sample in position relative to the functionalized particles, where, in examples, structures can include substrates (e.g., substrates patterned with the distribution of functionalized particles), microwells, microarrays (e.g., with nucleic acids capturing particles), scaffolds, or other 2D/3D structures. Additionally or alternatively, one or more of the sample and the functionalized particles can be retained in position by use of forces (e.g., magnetic forces, electrical forces/charged surfaces, gravitational forces, forces applied using acoustic or other vibration, centrifugal forces, buoyancy forces, chemical binding, etc.). In such variations, retention can be reversed by releasing retained functionalized particles from a support structure or substrate by one or more of: application of magnetic forces of reverse polarity or removal of a magnetic field (e.g., for functionalized magnetic particles), application of reverse polarity charge or other removal of electrical forces, removal of gravitational forces, removal of forces applied using acoustic or other vibration, application of a detergent to remove chemical bonds, and/or other suitable mechanisms. As such, retention and release of a sample from a substrate can be performed in a reversible or non-reversible manner (e.g., to facilitate enzymatic reactions at the substrate and/or within a process container after transfer of the substrate to the process container).

Figure 10:
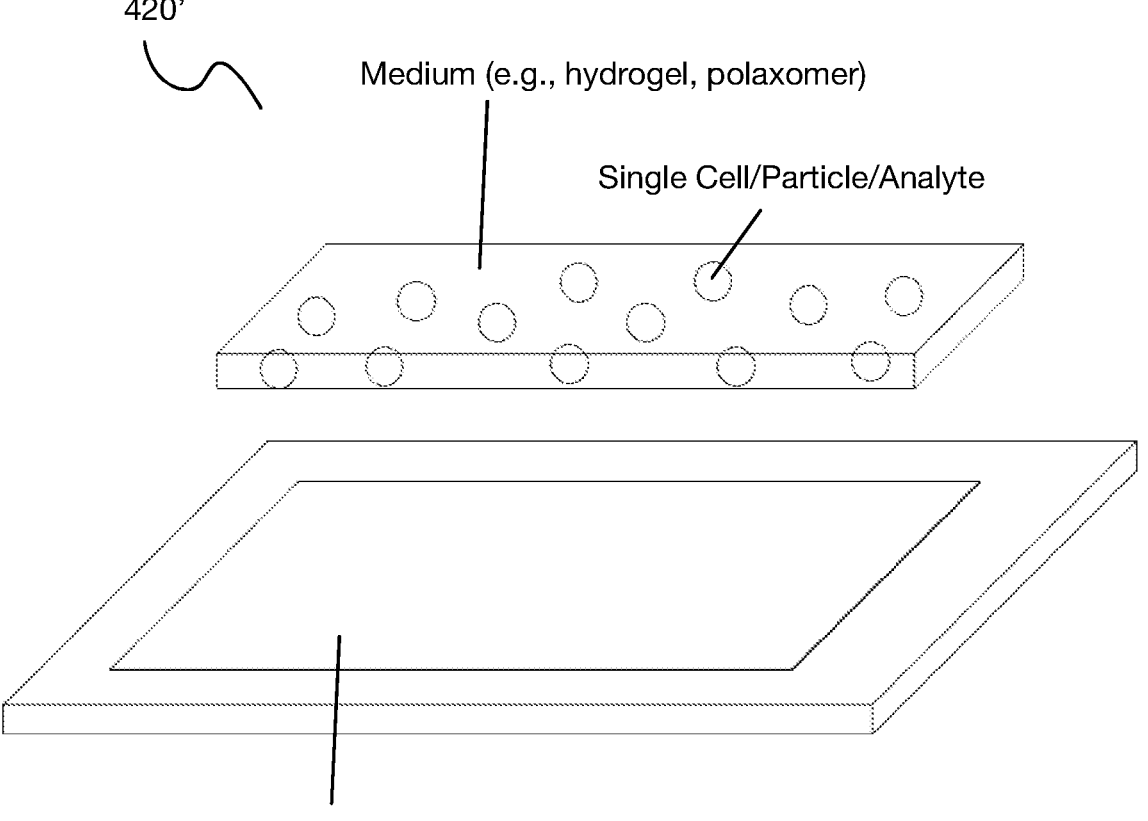
FIG. 10 depicts an example of processing steps associated with characterizing a distribution of single cells/particles/analytes dispersed across a medium or scaffold.

As shown in FIG. 10, a variation of receiving the sample at the substrate 420' can include receiving a composite sample, including a distribution of single cells (or alternatively, single particles, single, analytes, etc.) distributed within or across a medium (e.g., hydrogel medium, polaxomer medium), at the substrate, and performing embodiments, variations, and examples, of the method(s) described accordingly. Such a variation can thus enable single-cell or single particle spatial multi-omics without droplet-based or microwell-based systems, thereby producing shorter hands on time and/or less complex single-particle processing apparatus. Furthermore, such a variation can implement various substrate sizes in order to overcome doublet, triplet, quadruplet, etc. rates and increase throughput.

Additionally or alternatively, promoting interactions between functionalized particles of the system and a sample can include infusing functionalized particles and/or a system unit into or onto a sample (e.g., into a tissue, into an organ, etc.). Examples of infusion can include one or more of: injection, electroporation, use of vectors (e.g., viral vectors), and other infusion methods. Additionally or alternatively, Additionally or alternatively, promoting interactions between functionalized particles of the system and a sample can include coupling functionalized particles to a surface of a sample/specimen (e.g., by chemical binding, by magnetic binding, by other binding).

Additionally or alternatively, during use, and in an application of use involving spatial characterization of target analytes in 3D, stacks of substrates with distributions of functionalized particles can be implemented (e.g., with layering of samples/slices of tissue and units of the system 100, with disassembly of sample into sub-portions and interacting sub-portions with various substrates). As such, the system 100 can include additional substrates with distributions of functionalized particles (e.g., a second substrate with a second distribution of functionalized particles, a third substrate with a third distribution of functionalized particles, etc.), with layering or re-assembly of sample pieces and reconstruction of 3D volumes by stitching data derived from implementation of the various substrates.

Additionally or alternatively, during use, and in an application of use involving spatial characterization of target analytes in 3D, methods described can include applying units of the system 100 to a set of sides of a sample (e.g., block of tissue), followed by promoting interactions between the sample and functionalized particles of each unit of the system 100, and reconstructing 2D surfaces and/or 3D volumes by stitching data derived from implementation of the substrates of the units of the system 100. In variations, application of units of the system 100 to a set of sides of the sample can include providing a support structure 200 configured to fold about the set of sides of the sample (e.g., with an origami structure that folds to apply units of the substrate 110 to the set of sides of the sample, and unfolds to release the sample, etc.). Additionally or alternatively, the support structure 200 can be constructed with a shape memory material that responds to environmental conditions (e.g., temperature, electric field, pH, etc.) and adjusts morphology to contact the set of sides of the sample, and/or responds to environmental conditions (e.g., temperature, electric field, pH, etc.) and adjusts morphology to displace units of the system 100 from the set of sides of the sample (e.g., to release the sample for further processing). Such elements and configurations can thus be used to generate spatial distributions of targets of a sample, for samples that have a low level of rigidity. In examples, such tissues can have a Young's Modulus less than 50 kPa, less than 40 kPa, less than 30 kPa, 20 kPa, less than 15 kPa, less than 10 kPa, less than 9 kPa, less than 8 kPa, less than 7 kPa, less than 6 kPa, less than 5 kPa, less than 4 kPa, less than 3 kPa, less than 2 kPa, less than 1 kPa, or other suitable values. Additionally or alternatively, such elements and configurations can be used to generate spatial distributions of targets of a sample, for samples that have a high level of rigidity. In examples, such tissues can have a Young's Modulus greater than 50 kPa, greater than 100 kPa, greater than 1 MPa, greater than 50 MPa, greater than 100 MPa, greater than 500 MPa, greater than 1 GPa, greater than 10 GPa, greater than 20 GPa, greater than 30 GPa, greater than 40 GPa, greater than 50 GPa, greater than 60 GPa, greater than 70 GPa, greater than 80 GPa, greater than 90 GPa, greater than 100 GPa, or other suitable values.

Additionally or alternatively, the method can implement mapping molecules (e.g., delivered using a viral library encoding a diverse collection of RNA sequences) that interact with corresponding sample targets of the sample (e.g., through interactions with exposed target projection regions of the sample), and tracking the mapping molecules (e.g., through downstream sequencing processes) upon promoting an interaction between the sample and a unit of the system described above.

Additionally or alternatively, the method can implement structures (e.g., mesh structures with affinity molecules, mesh structures with primer-like sequences, etc.) positioned in proximity to a sample, where target analytes transfer to the structures during sample processing, and are subsequently processed using a unit of the system described above (e.g., by promoting interactions between the mesh structure and the unit of the system).

Steps 410 through 430 can implement embodiments of systems and support structures described above, and/or other suitable system elements, some embodiments, variations, and examples of which are described in U.S. application Ser. No. 17/376,396 incorporated by reference above.

Figure 9B:
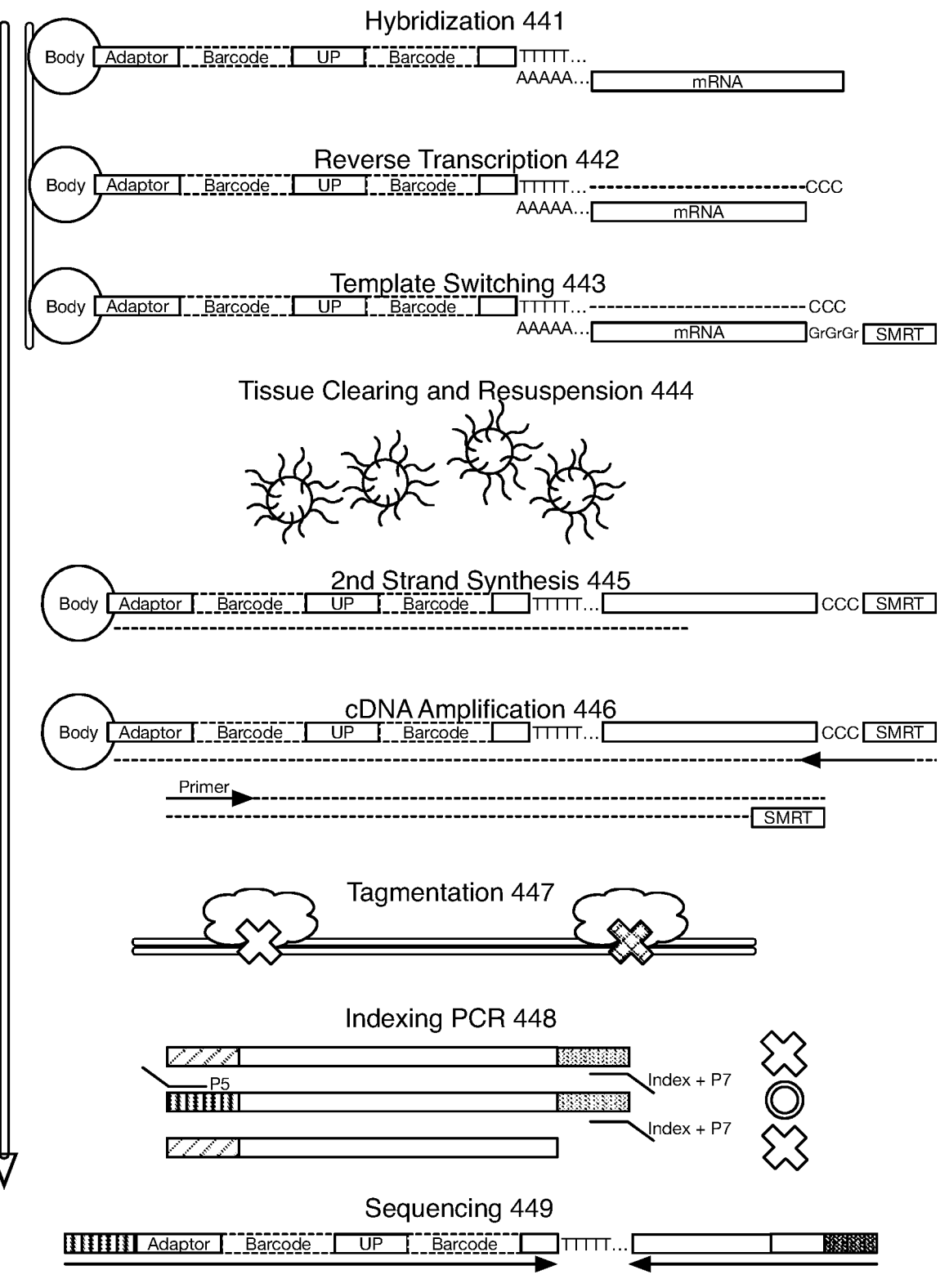
FIG. 9B depicts a schematic of an embodiment of a method for target characterization.

In some embodiments, as shown in FIG. 9B, applying a set of reactions to the sample at the substrate, can include performing a hybridization operation 441 between target material of the sample and the capture segments of the functionalized particles (e.g., at the substrate); performing a reverse transcription operation 442 upon outputs of the hybridization operation (e.g., at the substrate); performing a template switching operation 443 upon outputs of the reverse transcription operation (e.g., at the substrate); performing a tissue clearing operation with particle resuspension 444 (e.g., upon displacing the substrate after step 443 into the process container 250); performing a second strand synthesis operation 445 (e.g., within a process container 250); performing cDNA amplification operation 446 with outputs of the second strand synthesis operation 445 (e.g., within a process container 250); performing a tagmentation operation 447 with outputs of the cDNA amplification operation (e.g., within a process container 250); performing an indexing PCR operation 448 with outputs of the tagmentation operation (e.g., within a process container 250); and performing a sequencing operation 449 with outputs of the indexing PCR operation.

Variations of the set of reactions performed in step 440 can include one or more of: performing the second strand synthesis operation at the substrate (e.g., prior to or with omission of tissue clearing and particle resuspension); implementation of betaine, PEG or other molecular crowding agents, formamide, DMSO, and magnesium chloride for hybridization and reverse transcription operations; freezing the sample at the substrate post-application of the sample to the functionalized particles at the substrate, where freezing can be performed at a desired temperature (e.g., at 0° C., at −20° C., at −80° C., etc.) for a duration of time (e.g., 4 days, less than 4 days, more than 4 days) prior to performing subsequent processing steps (e.g., post-thaw) for target mapping, without significant degradation in particle robustness and mapping performance (e.g., in relation to performance and quality metrics described); implementation of terminal transferase enzyme (e.g., in TAS-seq) to generate a second strand (as an alternative to second strand synthesis as described); implementation for RNA fragmentation and A-tailing to capture more RNA material and/or desired regions of RNA material (e.g., non-coding, non-3' ends of mRNA material) of the sample (e.g., in VASA-seq); implementing immune repertoire VDJ assays (e.g., generating a VDJ recognition site) with template switching and long-read sequencing capabilities; performing probe-ligation for a targeted DNA panel assay, with permeabilization to access DNAs (e.g., using methanol fixation with permeabilization instead of other fixatives, with saponin, Triton X-100, NP40, Tween, etc.).

Variations of the reactions applied in step 440 can additionally or alternatively include executing an antibody-protein sequencing (Ab-seq) workflow with oligonucleotide-conjugated antibodies to examine protein expression. In one variation, the Ab-seq workflow can include performing a fixation operation (e.g., with formalin, with an alcohol such as methanol, etc.) and Ab-seq staining for the sample (e.g., a free-floating sample post-sectioning, a sample applied to a glass slide, a sample applied to a semi-permeable membrane or filter, etc.), followed by a hybridization operation with capture segments of functionalized particles (e.g., with maintenance of contact between the sample and the functionalized particles at the substrate). The Ab-seq workflow can include operations including: a polyA-based capture operation (or alternatively, a ligation-based capture operation), followed by a reverse transcription operation, a template switching operation, a tissue clearing operation, a second strand synthesis operation, a cDNA amplification operation (e.g., with Truseq/SMRT for mRNAs and Truseq/Abseq for AbOligonucleotides), separation of mRNA products from Ab-seq products by double sided cleanup, multiple rounds of PCR for AbOligonucleotide targets, and a tagmentation operation followed by indexing PCR for mRNA targets. Final PCR steps can be followed by next generation sequencing to combine RNA-seq and Ab-seq data outputs to characterize the sample.

Variations of the Ab-seq workflow can include one or more of: determining regions of interest (ROI) for examination by using registration features and/or fiducials to align a sample with the distribution of functionalized particles at the substrate (e.g., lining up sample features with registration features of the system 100 at the corners or other locations of the distribution of functionalized particles; dT blocking and de-blocking operations (e.g., at 55° C., with a washing step); performing Ab-seq with fluorophore staining (e.g., with Cy5 staining) as a quality control method for evaluating staining conditions and antibody titration); performing Ab-seq for adjacent sections, and performing stitching operations upon retrieved data in order to generate 3D characterizations of relevant biomarkers; performing Ab-seq with different stains for the same sample section; and performing other suitable operations.

In some embodiments, processing target analytes and characterization in steps 440 and 450 can include read-out/detection and identification of spatial labels/stochastic barcodes associated with target analytes by one or more of: sequencing (e.g., sequencing with error-reduction by dynamic annealing and ligation (SEDAL); sequencing by hybridization; sequencing by ligation; sequencing by polymerization; hybridization of fluorescent probes against barcode sequences (e.g., using Nanostring technology); PCR performing read-out operations of barcoded analytes (e.g., for applications with mRNA capture and next generation sequencing (NGS) read-out, for applications with reverse transcription followed by cDNA amplification followed by generation of NGS libraries, etc.); implementing documentation associating barcode sequences with locations of functionalized particles (e.g., by reading functionalized particle barcode sequences and transcript identities by NGS or other sequencing, then associate the barcode/transcript identities with the spatial location from the spatial decoding process performed during manufacturing); and performing other suitable steps. Identification of spatial labels/barcodes, in combination of detection of signals derived from target analytes captured at the distribution of functionalized particles can thus enable characterization of locations of the target analytes in space.

In variations, the method 400 can further include returning outputs based upon processing and characterization in steps 440 and 440. In example applications, returning outputs can include one or more of: returning an output characterizing a stage of cancer (e.g., upon identifying a set of cancer genes and/or spatial distributions thereof) associated with the sample; returning an output characterizing a somatic mutation associated with the sample; returning an output characterizing an immune response associated with the sample; returning an output characterizing a stage of biological development (e.g., development stage associated with clustering of mRNAs, etc.) associated with the sample; returning an output characterizing a pathological state (e.g., associated with liver disease, associated with kidney disease, associated with a neurological disease, associated with another disease state, performing diagnostics without whole transcriptome assessment etc.) associated with the sample; returning an output characterizing a spatial characteristics of a whole transcriptome associated with the sample; returning outputs characterizing gene expression of a targeted set of genes; returning outputs characterizing protein expression (e.g., via oligonucleotide-conjugated antibodies), returning outputs characterizing nucleosomal positioning (e.g., with ATAC-seq), returning outputs characterizing methylation sequences, returning outputs characterizing chromatin structure, returning outputs characterizing transcription factor binding, returning outputs characterizing genomic features (e.g., mutations, copy number variations, etc.), and/or returning other suitable outputs.

Additionally or alternatively, returned outputs and/or processing steps implemented according to the method 400 can be used to associate genotypic information with phenotypic information. In one example use case, (e.g., adapted from neuroscience applications), a phenotype of a target region can be controlled by optogenetics and/or observed in another suitable manner (e.g., using electrophysiology, using magnetic encephalography, etc.). The target region can then be analyzed with one or more units of the system to acquire spatial genomic information and to generate associations between phenotypic information and genomic information. Such methods can further be applied to other sample types, with or without stimulation of the sample.

As described, spatial characterization can be performed in 2D and/or 3D (e.g., with 3D structures and/or layering of system units with sample slices, etc.). Furthermore, a set of samples can be processed for a set of subjects/patients in parallel, using different subject/patient barcodes (e.g., molecular barcodes) in a manner that allows for decoding of characterizations corresponding to respective subjects/patients in an efficient manner.

The method 400 can include other suitable steps and/or enable other downstream applications.

5. Computer Systems

Figure 11:
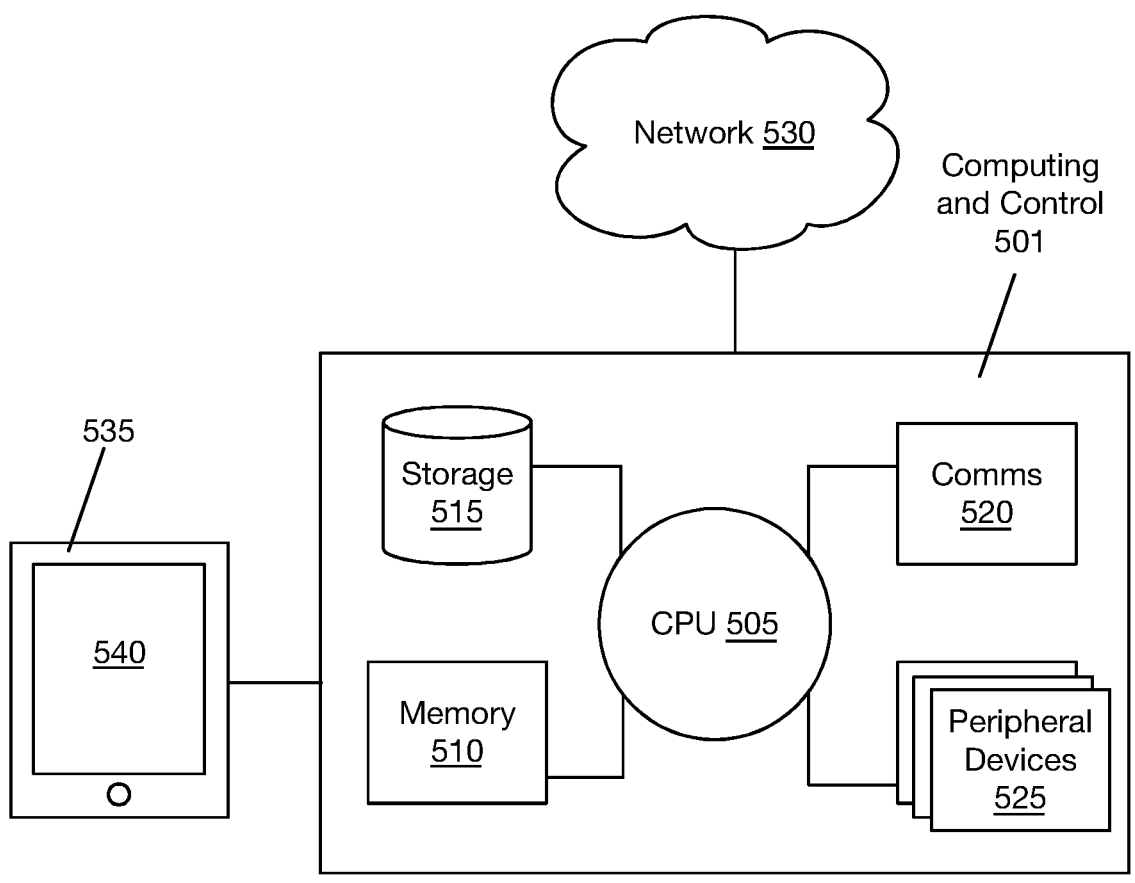
FIG. 11 illustrates a computer system that is programmed or otherwise configured to implement methods provided herein.

The present disclosure provides computer systems that are programmed to implement methods of the disclosure. FIG. 11 shows a computer system 501 that is programmed or otherwise configured to, for example, perform steps of methods for generating spatial maps of a distribution of targets of a sample, by one or more processes described.

The computer system 501 can regulate various aspects of analysis, calculation, and generation of the present disclosure, such as, for example, generating a spatial map of a distribution of targets of a sample by a set of processes, wherein the set of processes includes one or more of: receiving the sample at a substrate comprising a distribution of functionalized particles, each of the distribution of functionalized particles comprising a stochastic barcode sequence paired with a position on the substrate, promoting interactions between the distribution of targets of the sample, applying a set of reactions to the sample at the substrate, obtaining a set of sequences of a population of molecules generated from the set of reactions, the set of sequences associated with the distribution of targets labeled using the stochastic barcode sequences of the distribution of functionalized particles, and returning a set of positions of the distribution of targets upon processing the set of sequences. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet.

In some embodiments, the network 530 is a telecommunication and/or data network. The network 530 can include one or more computer servers, which can enable distributed computing, such as cloud computing. For example, one or more computer servers may enable cloud computing over the network 530 ("the cloud") to perform various aspects of analysis, calculation, and generation of the present disclosure, such as, for example, generating a plurality of droplets within a collecting container at a predetermined rate or variation in polydispersity. Such cloud computing may be provided by cloud computing platforms such as, for example, Amazon Web Services (AWS), Microsoft Azure, Google Cloud Platform, and IBM cloud. In some embodiments, the network 1130, with the aid of the computer system 501, can implement a peer-to-peer network, which may enable devices coupled to the computer system 101 to behave as a client or a server.

The CPU 505 may comprise one or more computer processors and/or one or more graphics processing units (GPUs). The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some embodiments, the circuit is an application specific integrated circuit (ASIC).

The storage unit 515 can store files, such as drivers, libraries and saved programs. The storage unit 515 can store user data, e.g., user preferences and user programs. In some embodiments, the computer system 501 can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 1101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some embodiments, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Embodiments of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, or disk drives, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, a visual display indicative of generating a spatial map of a distribution of targets of a sample by a set of processes, wherein the set of processes includes one or more of: receiving the sample at a substrate comprising a distribution of functionalized particles, each of the distribution of functionalized particles comprising a stochastic barcode sequence paired with a position on the substrate, promoting interactions between the distribution of targets of the sample, applying a set of reactions to the sample at the substrate, obtaining a set of sequences of a population of molecules generated from the set of reactions, the set of sequences associated with the distribution of targets labeled using the stochastic barcode sequences of the distribution of functionalized particles, and returning a set of positions of the distribution of targets upon processing the set of sequences. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, generate one or more spatial maps with performance characteristics described.

6. Conclusions

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or, if applicable, portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for whole transcriptome spatial analysis of a tissue sample, the method comprising:
   (a) receiving the tissue sample at a substrate comprising a distribution of functionalized particles,
       wherein each particle of the distribution of functionalized particles comprises an exonuclease-treated oligonucleotide comprising a stochastic barcode sequence paired with a position on the substrate, and
       wherein the distribution of functionalized particles is coupled to the substrate with a hydrophobic and electrostatic adhesive polymer layer comprising ethylene;
   (b) promoting interactions between target molecules of the tissue sample and the distribution of functionalized particles;
   (c) applying a set of reactions to the tissue sample at the substrate, wherein the tissue sample is not subjected to a permeabilization reaction;
   (d) obtaining a set of sequences of a population of molecules generated from the set of reactions, the set of sequences associated with the target molecules labeled using the stochastic barcode sequences of the distribution of functionalized particles;
   (e) returning a set of positions of the target molecules upon processing the set of sequences; and
   (f) generating a spatial map of a distribution of the target molecules based on the set of positions, wherein the spatial map is characterized by a signal-to-noise ratio (SNR) wherein the noise is minimized based on the non-permeabilized tissue sample.

2. The method of claim 1, wherein the tissue sample is comprises a frozen tissue sample.

3. The method of claim 1, wherein the set of reactions comprises hybridization between mRNA targets of the tissue sample and capture segments of the distribution of functionalized particles barcoded oligonucleotides.

4. The method of claim 1, wherein the spatial map comprises a resolution greater than 1 target per 50 $\mu m^2$.

5. The method of claim 1, wherein the spatial map comprises single cell resolution.

6. The method of claim 1, wherein the set of reactions comprises probe-ligation and permeabilization of the tissue sample.

7. The method of claim 1, wherein each particle of the distribution of functionalized particles further barcoded oligonucleotides comprises a photocleavable linker.

8. The method of claim 1, wherein the tissue sample comprises a formalin-fixed paraffin-embedded tissue sample comprising analytes modified to have a polyadenylated tail.

9. The method of claim 1, wherein the spatial map comprises a characterization of single cell subtypes of the tissue sample based upon an analysis of spatial marker genes represented by the set of sequences.

10. The method of claim 1, wherein the spatial map comprises a mapping of greater than 20,000 targets.

11. The method of claim 1, wherein at least one of the set of reactions of the tissue sample comprises obtaining a nuclei in suspension from the tissue sample.

12. The method of claim 1, wherein receiving the tissue sample at the substrate comprises aligning the tissue sample with the distribution of functionalized particles.

13. The method of claim 12, further comprising staining the tissue sample.

14. The method of claim 1, wherein the SNR is determined by:

identifying a gene with a known expression profile across regions of the tissue sample, wherein the target molecules comprise the gene;

quantifying expression of the gene across the tissue sample based upon the set of positions of the distribution of the target molecules;

determining a signal value from expression of the gene in regions of the tissue sample that should express the gene, based upon the known expression profile;

determining a noise value from expression of the gene in regions of the tissue sample that should not express the gene, based upon the known expression profile; and determining the SNR from the signal value and the noise value.

15. The method of claim 1, wherein capture segments of each of the exonuclease-treated oligonucleotides comprise polyT sequences.

16. The method of claim 1, wherein the distribution of functionalized particles barcoded oligonucleotides are attached to an intermediate particle layer, and wherein the intermediate particle layer is distributed onto the substrate.

17. The method of claim 1, wherein the hydrophobic and electrostatic adhesive polymer layer is to an intermediate particle layer distributed onto a glass substrate.

18. The method of claim 1, further comprising freezing the tissue sample at the substrate after receiving the tissue sample at the substrate.

* * * * *